US011001901B1

(12) United States Patent
Donati et al.

(10) Patent No.: US 11,001,901 B1
(45) Date of Patent: May 11, 2021

(54) METHODS AND REAGENTS FOR THE SPECIFIC AND SENSITIVE DETECTION OF SARS-COV-2

(71) Applicant: INSTITUT PASTER, Paris (FR)

(72) Inventors: Flora Donati, Paris (FR); Mélanie Albert, Paris (FR); Sylvie Behillil, Paris (FR); Vincent Enouf, Paris (FR); Sylvie van der Werf, Paris (FR)

(73) Assignee: INSTITUT PASTEUR, Paris (FR)

( * ) Notice: Subject to any disclaimer, the term of this patent is extended or adjusted under 35 U.S.C. 154(b) by 0 days.

(21) Appl. No.: 16/809,717

(22) Filed: Mar. 5, 2020

(51) Int. Cl.
*C12Q 1/68* (2018.01)
*C12Q 1/70* (2006.01)
*C12N 15/10* (2006.01)

(52) U.S. Cl.
CPC ......... *C12Q 1/701* (2013.01); *C12N 15/1096* (2013.01)

(58) Field of Classification Search
CPC ...................................................... C12Q 1/68
See application file for complete search history.

(56) References Cited

PUBLICATIONS

Corman et al., Detection of 2019 novel coronavirus (2019-nCoV) by real-time RT-PCR, Euro Surveill. Jan. 23, 2020; 25(3): 2000045.*
Sheikhzadeh et al., Diagnostic techniques for COVID-19 and new developments, Talanta. Dec. 1, 2020;220:121392. doi: 10.1016/j.talanta.2020.121392. Epub Jul. 14, 2020.*
International Searching Authority in International Application No. PCT/EP2020/055939, dated Nov. 19, 2020.
Who Team: "Molecular assays to diagnose COVID-19: Summary table of available protocols", Jan. 24, 2020 (Jan. 24, 2020), XP055732018, Retrieved from the Internet: URL:https://www.who.int/docs/default-source/coronaviruse/whoinhouseassays.pdf?sfvrsn=de3a76aa 2&download=true [retrieved on Sep. 18, 2020].
Victor M Corman et al: "Detection of 2019 novel coronavirus (2019-nCoV) by real-time RT-PCR", Eurosurveillance, vol. 25, No. 3, Jan. 23, 2020 (Jan. 23, 2020), XP055695049.

* cited by examiner

*Primary Examiner* — Aaron A Priest
(74) *Attorney, Agent, or Firm* — Arrigo, Lee, Guttman & Mouta-Bellum LLP

(57) ABSTRACT

Methods, primers, sets of primers, probes, compositions, and kits for detecting presence or absence of SARS-CoV-2 in a sample are provided.

9 Claims, No Drawings

Specification includes a Sequence Listing.

METHODS AND REAGENTS FOR THE SPECIFIC AND SENSITIVE DETECTION OF SARS-COV-2

FIELD OF THE INVENTION

The invention relates to methods and reagents to detect the presence and/or absence of the 2019 novel coronavirus (SARS-CoV-2, 2019-nCov or COVID-19) in a sample. The methods and reagents are useful for screening samples for presence and/or absence of SARS-CoV-2 and may therefore be used to screen subjects to identify individuals infected with SARS-CoV-2, among other uses.

BACKGROUND OF THE INVENTION

In December 2019, patients presenting with viral pneumonia were reported in Wuhan, China. A novel coronavirus was subsequently identified as the causative agent, and provisionally named 2019 novel coronavirus (2019-nCov or SARS-CoV-2) (Zhu N et al., N Engl J Med., 2020 Jan. 24). The virus swiftly spread within and outside China, leading to the WHO declaring a Public Health Emergency of International Concern on Jan. 30, 2020. With the aim of rapid development of an assay for detection of the presence and/or absence of SARS-CoV-2 in a sample, and based on state of the art real-time RT-PCR technology, two targets in the RNA-dependent RNA polymerase (RdRP) gene of the virus were identified herein by the inventors.

Coronaviruses are enveloped, positive single stranded RNA viruses. Coronaviruses have been identified in various mammalians hosts such as bats, camels, or mice, among others. Several coronaviruses are pathogenic to humans, leading to varying severity of symptoms (Cui et al., Nat Rev Microbiol. 2019 March; 17(3):181-92). Highly pathogenic variants include the severe acute respiratory syndrome coronavirus (SARS-Cov) that emerged in China in 2002, resulting in ~8000 human infections and 700+ deaths (Peiris et al., Nat Med., 2004 December; 10(12 Suppl):S88-97) and the Middle East respiratory syndrome coronavirus (MERS-CoV), first detected in Saudi Arabia in 2012 and responsible for ~2500 human infections and 850+ deaths (Zaki et al., N Engl J Med., 2012 Nov. 8; 367(19):1814-20; Lee et al., BMC Infect Dis. 2017 Jul. 14; 17(1):498).

Coronavirus genomes encodes non-structural polyprotein and structural proteins, including the Spike (S), envelope, membrane and nucleocapsid proteins. The coronavirus RNA genome has a 5' methylated cap and a 3' polyadenylated tail, which allows the RNA to attach to the host cell's ribosome for translation. Coronavirus genomes encode a protein called RNA-dependent RNA polymerase (RdRp), which allows the viral genome to be transcribed into new RNA copies using the host cell's machinery. The RdRp is the first protein to be made; once the gene encoding the RdRp is translated, translation is stopped by a stop codon. RNA-dependent RNA polymerase (RdRp, RDR) is an enzyme that catalyzes the replication of RNA from an RNA template. This is in contrast to a typical DNA-dependent RNA polymerase, which catalyzes the transcription of RNA from a DNA template. RdRP is an essential protein encoded in the genomes of all RNA-containing viruses with no DNA stage. It catalyzes synthesis of the RNA strand complementary to a given RNA template. The RNA replication process is a two-step mechanism. First, the initiation step of RNA synthesis begins at or near the 3' end of the RNA template by means of a primer-independent (de novo), or a primer-dependent mechanism that utilizes a viral protein genome-linked (VPg) primer. The de novo initiation consists in the addition of a nucleoside triphosphate (NTP) to the 3'-OH of the first initiating NTP. During the following so-called elongation phase, this nucleotidyl transfer reaction is repeated with subsequent NTPs to generate the complementary RNA product.

There is an urgent need for new methods and reagents to identify with specificity and improved sensitivity the presence and/or absence of SARS-CoV-2 in samples. This invention as depicted hereinafter was designed and tested by the National Reference Center for Respiratory Virus, Institut Pasteur Paris, in panels of patients in France suspected to be infected by SARS-CoV-2 or in close contact with individuals known to be infected by SARS-CoV-2. Following the results, this PCR test showed 100% positive detection of about at least as low as 100 copies of target RNA per reaction in singleplex or 10 copies in multiplex using the selected 2 pairs of primers described below. This test is not reactive to other coronavirus, nor to other viruses causing respiratory infections, and distress in some patients. This test which is now validated on a panel of SARS-CoV-2 of 600 positive and negative patients, including asymptomatic contact individuals, individuals returning from epidemic zone, and symptomatic patients. Within symptomatic patients, as there is also a concurrent epidemic of flu in France, negative patients with the SARS-CoV2 test of the invention were confirmed to be infected by flu or other respiratory diseases. The validation of this test will now allow dispatch for diagnosis to reference hospitals in France and abroad, and within the international network of Institut Pasteur around the world.

SUMMARY OF THE INVENTION

The inventors have designed methods and reagents comprising novel nucleic acids that may be used as primers and/or probes, and are based in part on the inventors' discovery that these nucleic acids enable detection of the presence and/or absence of SARS-CoV-2 with very desirable sensitivity and specificity.

In a first aspect the invention provides a first method for detecting the presence or absence of a SARS-CoV-2 RNA in a sample, comprising: providing a sample; subjecting the sample to a reverse transcription reaction with a SARS-CoV-2-specific reverse primer to generate specific cDNA copy of SARS-CoV-2 RNA in the sample, wherein the reverse primer hybridizes to the sequence: 5'-ACAACACAACAAAGGGAG-3' (SEQ ID NO:11) and the RNA equivalent thereof; amplifying any resultant cDNA; and detecting any amplified product with a probe that hybridizes to the sequence: 5'-TACCGGCAGCACAA-GACATCT-3' (SEQ ID NO:12) or the complement thereof. In some embodiments, the resultant cDNA is amplified with the reverse primer and a forward primer, wherein the forward primer hybridizes to the sequence: 5'-CAACAGGACTAAGCTCAT-3' (SEQ ID NO: 10).

In a preferred embodiment of the method, the reverse primer comprises the sequence 5' CTCCCTTTGTTGTGTTGT-3' (SEQ ID NO: 2), or a variant thereof, and is from 15 to 21 bases in length; and/or the forward primer comprises the sequence 5' ATGAGCT-TAGTCCTGTTG-3' (SEQ ID NO: 1), or a variant thereof, and is from 15 to 21 bases in length; and/or the probe comprises the sequence 5' AGATGTCTTGTGCTGCCGGTA 3' (SEQ ID NO: 3), or a variant thereof, or the complement of either of these, and is from 18 to 24 bases in length.

In a more preferred embodiment of the method, the reverse primer consists of the sequence 5' CTCCCTTTGTTGTGTTGT-3' (SEQ ID NO: 2); and/or the forward primer consists of the sequence 5' ATGAGCT-TAGTCCTGTTG-3' (SEQ ID NO: 1); and/or the probe consists of the sequence 5' AGATGTCTTGTGCTGCCGGTA 3' (SEQ ID NO: 3), or the complement thereof.

In a still more preferred embodiment of the method, the reverse primer consists of the sequence 5' CTCCCTTTGTTGTGTTGT-3' (SEQ ID NO: 2); the forward primer consists of the sequence 5' ATGAGCT-TAGTCCTGTTG-3' (SEQ ID NO: 1); and the probe consists of the sequence 5' AGATGTCTTGTGCTGCCGGTA 3' (SEQ ID NO: 3), or the complement thereof.

In another aspect the invention provides a second method for detecting the presence or absence of a SARS-CoV-2 RNA in a sample, comprising: providing a sample; subjecting the sample to a reverse transcription reaction with a specific reverse primer to generate a cDNA copy of SARS-CoV-2 RNA in the sample, wherein the reverse primer hybridizes to the sequence: 5'-CCTATAT-TAACCTTGACCAG-3' (SEQ ID NO:14) and the RNA equivalent thereof; amplifying any resultant cDNA; and detecting any amplified product with a probe that hybridizes to the sequence: 5'-CCTGGCGTGGTTTGTATGA-3' (SEQ ID NO:15) or the complement thereof. In some embodiments, the resultant cDNA is amplified with the reverse primer and a forward primer, wherein the forward primer hybridizes to the sequence: 5'-CGAAATCATACCAGT-TACC-3' (SEQ ID NO:13).

In a preferred embodiment of the second method, the reverse primer comprises the sequence 5' CTGGT-CAAGGTTAATATAGG-3' (SEQ ID NO: 5), or a variant thereof, and is from 17 to 23 bases in length; and/or the forward primer comprises the sequence 5' GGTAACTGGTATGATTTCG-3' (SEQ ID NO: 4), or a variant thereof, and is from 16 to 22 bases in length; and/or the probe comprises the sequence 5' TCATACAAAC-CACGCCAGG 3' (SEQ ID NO: 6), or a variant thereof, or the complement of either of these, and is from 16 to 22 bases in length.

In a more preferred embodiment of the method, the reverse primer consists of the sequence 5' CTGGT-CAAGGTTAATATAGG-3' (SEQ ID NO: 5); and/or the forward primer consists of the sequence 5' GGTAACTGGTATGATTTCG-3' (SEQ ID NO: 4); and/or the probe consists of the sequence 5' TCATACAAAC-CACGCCAGG 3' (SEQ ID NO: 6), or the complement thereof.

In a still more preferred embodiment of the second method, the reverse primer consists of the sequence 5' CTGGTCAAGGTTAATATAGG-3' (SEQ ID NO: 5); the forward primer consists of the sequence 5' GGTAACTGGTATGATTTCG-3' (SEQ ID NO: 4); and the probe consists of the sequence 5' TCATACAAAC-CACGCCAGG 3' (SEQ ID NO: 6), or the complement thereof.

In another aspect the invention provides a third method for detecting the presence or absence of a SARS-CoV-2 RNA in a sample. The third method combines the first and second methods to provide a combinatorial assay.

In another aspect the invention provides a fourth method for detecting the presence or absence of a SARS-CoV-2 RNA in a sample, comprising: providing a sample; subjecting the sample to a reverse transcription reaction with a SARS-CoV-2 specific reverse primer to generate a cDNA copy RNA in the sample; amplifying any resultant DNA with the reverse primer and a SARS-CoV-2 specific forward primer, wherein the reverse and forward primers amplify a target sequence of SARS-CoV-2 RNA selected from the group consisting of the sequences SEQ ID NO: 16 and SEQ ID NO: 17 and the variants thereof comprising the addition of up to 20 consecutive nucleotides of 5' and/or 3' flanking sequence from said SARS-CoV-2 RNA or the deletion of up to 20 consecutive nucleotides at one or both ends of said sequences; and detecting any amplified product with a SARS-CoV-2 specific probe. In some embodiments, the forward and reverse primer and the probe are as described above for the first and second method. In some embodiments, the method combines the amplification of the target sequence SEQ ID NO: 16 or a variant thereof and the target sequence SEQ ID NO: 17 or a variant thereof.

In some embodiments, the method is an RT-PCR method.

In some embodiments, the method comprises reverse transcribing and amplifying an internal positive control. In a preferred embodiment, the internal positive control reverse primer comprises the sequence 5' ATAT-TGCAGCAGTACGCACACA-3' (SEQ ID NO: 8), or a variant thereof, and is from 19 to 25 bases in length; and/or the internal positive control forward primer comprises the sequence 5' ACAGGTACGTTAATAGTTAATAGCGT-3' (SEQ ID NO: 7), or a variant thereof, and is from 23 to 29 bases in length; and/or the internal positive control probe comprises the sequence 5' ACACTAGCCATCCT-TACTGCGCTTCG 3' (SEQ ID NO: 9), or a variant thereof, or the complement of either of these, and is from 23 to 29 bases in length.

In some embodiments of the methods, the probe and the internal positive control probe are labelled with 6-carboxy-fluorescein (6FAM) or hexachloro-6-carboxy-fluorescein (HEX) at the 5' end.

In some embodiments of the methods, the probe and the internal positive control probe are labelled with black hole quencher 1 (BHQ1) at the 3' end.

In some embodiments of the methods, the coronavirus is SARS-CoV-2 and is not other conoravirus, nor other viruses causing respiratory diseases.

In another aspect the invention provides a primer for use in the amplification of a SARS-CoV-2 RNA in a sample, wherein the primer: hybridizes to the sequence: 5'-ACAACACAACAAAGGGAG-3' (SEQ ID NO:11) and the RNA equivalent thereof; hybridizes to the sequence: 5'-CAACAGGACTAAGCTCAT-3' (SEQ ID NO:10); hybridizes to the sequence: 5'-CCTATAT-TAACCTTGACCAG-3' (SEQ ID NO:14) and the RNA equivalent thereof; or hybridizes to the sequence: 5'-CGAAATCATACCAGTTACC-3' (SEQ ID NO:13).

In a preferred embodiment, the primer comprises the sequence 5' CTCCCTTTGTTGTGTTGT-3' (SEQ ID NO: 2), or a variant thereof, and is from 15 to 21 bases in length; comprises the sequence 5' ATGAGCTTAGTCCTGTTG-3' (SEQ ID NO: 1), or a variant thereof, and is from 15 to 21 bases in length; comprises the sequence 5' CTGGT-CAAGGTTAATATAGG-3' (SEQ ID NO: 5), or a variant thereof, and is from 17 to 23 bases in length; or comprises the sequence 5' GGTAACTGGTATGATTTCG-3' (SEQ ID NO: 4), or a variant thereof, and is from 16 to 22 bases in length.

In a more preferred embodiment, the primer consists of the sequence 5' CTCCCTTTGTTGTGTTGT-3' (SEQ ID NO: 2); consists of the sequence 5'-ATGAGCT-TAGTCCTGTTG-3' (SEQ ID NO: 1); consists of the sequence 5'-CTGGTCAAGGTTAATATAGG-3' (SEQ ID NO: 5); or consists of the sequence 5'-GGTAACTGGTAT-GATTTCG-3' (SEQ ID NO: 4).

In another aspect the invention provides a set of primers for use in the amplification of a SARS-CoV-2 RNA in a sample, wherein the primer set comprises: a first primer that hybridizes to the sequence: 5'-ACAACACAACAAAGG-GAG-3' (SEQ ID NO:11) and the RNA equivalent thereof; and a second primer that hybridizes to the sequence: 5'-CAACAGGACTAAGCTCAT-3' (SEQ ID NO:10).

In a preferred embodiment, primer set comprises: a first primer comprising the sequence 5' CTCCCTTTGTTGTGTTGT-3' (SEQ ID NO: 2), or a variant thereof, that is from 15 to 21 bases in length; and a second primer comprising the sequence 5' ATGAGCT-TAGTCCTGTTG-3' (SEQ ID NO: 1), or a variant thereof, that is from 15 to 21 bases in length.

In a more preferred embodiment, the first primer consists of the sequence 5' CTCCCTTTGTTGTGTTGT-3' (SEQ ID NO: 2); and the second primer consists of the sequence 5' ATGAGCTTAGTCCTGTTG-3' (SEQ ID NO: 1).

In another aspect, the invention provides an alternative set of primers, wherein the primer set comprises: a first primer that hybridizes to the sequence: 5'-CCTATAT-TAACCTTGACCAG-3' (SEQ ID NO:14) and the RNA equivalent thereof; and a second primer that hybridizes to the sequence: 5' CGAAATCATACCAGTTACC-3' (SEQ ID NO:13).

In a preferred embodiment, the primer set comprises: a first primer comprising the sequence 5'-CTGGTCAAGGT-TAATATAGG-3' (SEQ ID NO: 5), or a variant thereof, and is from 17 to 23 bases in length; or a second primer comprising the sequence 5' GGTAACTGGTATGATTTCG-3' (SEQ ID NO: 4), or a variant thereof, and is from 16 to 22 bases in length.

In a more preferred embodiment, the first primer consists of the sequence 5'-CTGGTCAAGGTTAATATAGG-3' (SEQ ID NO: 5); and the second primer consists of the sequence 5'-GGTAACTGGTATGATTTCG-3' (SEQ ID NO: 4).

In another aspect, the invention provides an alternative set of primers, for use in the amplification of a SARS-CoV-2 RNA in a sample, wherein the primer set comprises: a first primer that hybridizes to the sequence: 5'-ACAACACAACAAAGGGAG-3' (SEQ ID NO:11) and the RNA equivalent thereof; a second primer that hybridizes to the sequence: 5'-CAACAGGACTAAGCTCAT-3' (SEQ ID NO:10); a third primer that hybridizes to the sequence: 5'-CCTATATTAACCTTGACCAG-3' (SEQ ID NO:14) and the RNA equivalent thereof; and a fourth primer that hybridizes to the sequence: 5' CGAAATCATACCAGTTACC-3' (SEQ ID NO:13).

In a preferred embodiment, the primer set comprises: a first primer comprising the sequence 5' CTCCCTTTGTTGTGTTGT-3' (SEQ ID NO: 2), or a variant thereof, that is from 15 to 21 bases in length; a second primer comprising the sequence 5' ATGAGCT-TAGTCCTGTTG-3' (SEQ ID NO: 1), or a variant thereof, that is from 15 to 21 bases in length; a third primer comprising the sequence 5' CTGGTCAAGGT-TAATATAGG-3' (SEQ ID NO: 5), or a variant thereof, and is from 17 to 23 bases in length; and a fourth primer comprising the sequence 5' GGTAACTGGTATGATTTCG-3' (SEQ ID NO: 4), or a variant thereof, and is from 16 to 22 bases in length.

In a preferred embodiment, the first primer consists of the sequence 5' CTCCCTTTGTTGTGTTGT-3' (SEQ ID NO: 2); the second primer consists of the sequence 5'-ATGAGCTTAGTCCTGTTG-3' (SEQ ID NO: 1); the third primer consists of the sequence 5'-CTGGTCAAGGT-TAATATAGG-3' (SEQ ID NO: 5); and the fourth primer consists of the sequence 5' GGTAACTGGTATGATTTCG-3' (SEQ ID NO: 4).

In another aspect the invention provides a set of primers for use in in the specific amplification of SARS-CoV-2 RNA in a sample, which comprises a SARS-CoV-2-specific forward primer and reverse primer which amplify the sequence SEQ ID NO: 16 or 17 or a variant thereof comprising the addition of up to 20 consecutive nucleotides of 5' and/or 3' flanking sequence from SARS-CoV-2 RNA or the deletion of up to 20 consecutive nucleotides at one or both ends of said sequences.

In another aspect, the invention provides a probe for use in the detection of amplification products of a SARS-CoV-2 RNA in a sample, wherein the probe hybridizes to the sequence: 5'-TACCGGCAGCACAAGACATCT-3' (SEQ ID NO:12) or the complement thereof; or wherein the probe hybridizes to the sequence: 5'-CCTGGCGTGGTTTGTATGA-3' (SEQ ID NO:15) or the complement thereof.

In a preferred embodiment, the probe comprises the sequence 5' AGATGTCTTGTGCTGCCGGTA 3' (SEQ ID NO: 3), or a variant thereof, or the complement of either of these, and is from 18 to 24 bases in length; or the probe comprises the sequence 5' TCATACAAACCACGCCAGG 3' (SEQ ID NO: 6), or a variant thereof, or the complement of either of these, and is from 16 to 22 bases in length.

In a more preferred embodiment, the probe consists of the sequence 5' AGATGTCTTGTGCTGCCGGTA 3' (SEQ ID NO: 3), or the complement thereof; or the probe consists of the sequence 5' TCATACAAACCACGCCAGG 3' (SEQ ID NO: 6), or the complement thereof.

In some embodiments the probe is labelled with 6-carboxy-fluorescein (6FAM) or hexachloro-6-carboxy-fluorescein (HEX) at the 5' end.

In some embodiments the probe is labelled with black hole quencher 1 (BHQ1) at the 3' end.

Also provided is a composition comprising a set of primers as described herein and a probe as described herein.

Also provided is a kit comprising a set of primers as described herein and a probe as described herein. In some embodiments the kit further comprises an internal negative control. In some embodiments the kit further comprises an internal positive control. In a preferred embodiment, the internal positive control comprises: a reverse primer comprising the sequence 5' ATAT-TGCAGCAGTACGCACACA-3' (SEQ ID NO: 8), or a variant thereof, that is from 19 to 25 bases in length; and/or a forward primer comprising the sequence 5' ACAGGTACGTTAATAGTTAATAGCGT-3' (SEQ ID NO: 7), or a variant thereof, that is from 23 to 29 bases in length; and/or a probe comprising the sequence 5' ACACTAGC-CATCCTTACTGCGCTTCG 3' (SEQ ID NO: 9), or a variant thereof, or the complement of either of these, that is from 23 to 29 bases in length.

In some embodiments the kit further comprises a reverse transcriptase.

In some embodiments the kit further comprises a DNA polymerase.

In some embodiments the kit further comprises dNTPs.

In preferred embodiments of the primer, set of primers, probe, composition, or kit is specific to SARS-CoV-2.

DETAILED DESCRIPTION OF THE INVENTION

As used herein a "variant" of a reference sequence of nucleotides is a modified form in which at least one nucleotide is added, deleted, or substituted. In some embodiments the variant includes only addition of one or more nucleotides. In some embodiments the variant includes only deletion of one or more nucleotides. In some embodiments the variant includes only substitution of one or more nucleotides. In some embodiments the variant includes addition and deletion of different nucleotides. An addition is a change that increases the total number of nucleotides in the sequence while a deletion is a change that decreases the total number of nucleotides. In some embodiments the addition and/or deletion occurs at only one end while in other embodiments it occurs at both ends. In some embodiments an addition or deletion is internal. In some embodiments the variant includes only one nucleotide that is added, deleted, or substituted. In some embodiments 2, 3, 4, 5, 6, 7, 8, 9 or 10 or more nucleotides are added, deleted, or substituted. A variant according to the invention hybridizes to SARS-CoV-2 nucleic acid (RNA, DNA equivalent or complement thereof). In this context, the term "hybridizes to" refers to the ability of the variant to form a double-stranded hybrid molecule with SARS-CoV-2 nucleic acid.

According to standard practice in the field of virology, the sequences of coronavirus genome (positive single stranded RNA) or fragments thereof (target sequences for SARS-CoV-2 RNA amplification) are disclosed in the DNA form. Therefore, the sequence SEQ ID NO: 19 is the DNA equivalent of SARS-CoV-2 RNA and the sequences SEQ ID NO: 16 and SEQ ID NO: 17 are the DNA equivalent of SARS-CoV-2 RNA target sequences for SARS-CoV-2 RNA amplification.

SARS-CoV-2 Nucleic Acid Sequences

Based on the first sequences of SARS-CoV-2 made available on the GISAID database on Jan. 11, 2020 (SEQ ID NO: 19), primers and probes (nCoV_IP2 and nCoV_IP4) were designed to target the RdRp gene spanning nt 12621-12727 and 14010-14116 (positions according SARS-CoV, NC_004718). These positions correspond to nt 12669-12776 and 14059-14165 in SARS-CoV-2 sequence (SEQ ID NO: 19).

The following table lists preferred embodiments of SARS-CoV-2 nucleic acid sequences of this disclosure, which were identified by the inventors as described in the examples. The primer/probe column lists the sequences of the forward primer, reverse primer, and probe used in the Example. The Target Sequence (reverse complement) column lists the reverse complement (i.e., target) of the primer/probe sequence. The sequences are represented as DNA but in alternative embodiments at least one of the nucleotides may be an RNA nucleotide.

Methods for Detection

The invention encompasses methods for specific detection of SARS-CoV-2. In one embodiment, the method comprises providing a sample, subjecting the sample to a reverse transcription reaction to generate a cDNA copy SARS-CoV-2 RNA in the sample using a "reverse primer" specific for coronavirus, amplifying any resultant DNA with the "reverse primer" and a "forward primer," and detecting any amplified product with a "probe." The method can be used for the determination of whether or not SARS-CoV-2 is present in the sample.

In some embodiments, the sample is an environmental sample, such as soil, food, beverages, feed, water (e.g., fresh water, salt water, waste water, and drinking water), sewage, sludge, and surfaces or samples obtained from surface swipes. In preferred embodiments, the sample is a biological sample, for example, stool, saliva, blood, plasma, serum, urine, cerebrospinal fluid, or tissue sample.

The sample can be subjected to well-known isolation and purification protocols or used directly. For example, the sample can be subjected to a treatment to release/extract the nucleic acids of the sample and/or to remove proteins and other non-nucleic acid components of the sample using conventional techniques, such as those in the Examples.

Reverse transcription of the RNA of a coronavirus strain can be performed with a "reverse primer" specific for coronavirus. A "reverse primer" is one that, based on its 5'-3' orientation, can bind to a single-stranded RNA and serve to initiate generation of a complementary DNA (cDNA) copy of the RNA. The reverse transcription can be accomplished using well known and routine methods. The reaction mix for reverse transcription contains the reagents for the reaction, for example, a reverse primer, dNTPs (dATP, dCTP, dGTP and dTTP), a buffer, and a reverse transcriptase. Exemplary reaction conditions are set forth in the examples.

Amplification of the cDNA copy of a coronavirus strain generated by reverse transcription can be performed with a "forward primer" specific for coronavirus. A "forward primer" is one that, based on its 5'-3' orientation, can bind to a single-stranded antisense cDNA copy of an RNA generated by reverse transcription and serve to initiate generation of a double-stranded DNA copy of the RNA. The amplification can be accomplished using well known and routine methods. The reagent mix for amplification contains the reagents for the reaction, for example a forward primer, a reverse primer, dNTPs, a buffer, and a DNA polymerase.

|  | Primer/Probe | Target Sequence (reverse complement) |
|---|---|---|
| RdRp gene/nCoV_IP2 | | |
| nCoV_IP2-12669Fw | ATGAGCTTAGTCCTGTTG (SEQ ID NO: 1) | CAACAGGACTAAGCTCAT (SEQ ID NO: 10) |
| nCoV_IP2-12759Rv | CTCCCTTTGTTGTGTTGT (SEQ ID NO: 2) | ACAACACAACAAAGGGAG (SEQ ID NO: 11) |
| nCoV_IP2-12696bProbe(+) | AGATGTCTTGTGCTGCCGGTA (SEQ ID NO: 3) | TACCGGCAGCACAAGACATCT (SEQ ID NO: 12) |
| RdRp gene/nCoV_IP4 | | |
| nCoV_IP4-14059Fw | GGTAACTGGTATGATTTCG (SEQ ID NO: 4) | CGAAATCATACCAGTTACC (SEQ ID NO: 13) |
| nCoV_IP4-14146Rv | CTGGTCAAGGTTAATATAGG (SEQ ID NO: 5) | CCTATATTAACCTTGACCAG (SEQ ID NO: 14) |
| nCoV_IP4-14084Probe(+) | TCATACAAACCACGCCAGG (SEQ ID NO: 6) | CCTGGCGTGGTTTGTATGA (SEQ ID NO: 15) |

In one embodiment, the method of the invention is performed using a single RT-PCR reagent mix containing the reagents for the reverse transcription and amplification reactions. Preferably, the reverse primer used for the reverse transcription reaction is also used for the amplification reaction.

Preferably, the reverse transcription and amplification reactions are performed in a plastic or glass container, most preferably in the same container.

Amplification methods known in the art include RCA, MDA, NASBA, TMA, SDA, LCR, b-DNA, PCR (all forms including RT-PCR), RAM, LAMP, ICAN, SPIA, QB-replicase, or Invader. A preferred amplification method is the polymerase chain reaction (PCR) amplification. See, e.g., PCR Technology: Principles and Applications for DNA Amplification (Ed. H. A. Erlich, Freeman Press, NY, N.Y., 1992); PCR Protocols: A Guide to Methods and Applications (Eds. linis, et al., Academic Press, San Diego, Calif., 1990); Mattila et al., Nucleic Acids Res. 19, 4967 (1991); Eckert et al., PCR Methods and Applications 1, 17 (1991); PCR (Eds. McPherson et al., IRL Press, Oxford); and U.S. Pat. Nos. 4,683,202, 4,683,195, 4,800,159 4,965,188, and 5,333,675. More preferred PCR methods is real-time PCR, PCR-HRM (High-Resolution DNA Melting) (see Andriantsoanirina et al. Journal of Microbiological Methods, 78: 165 (2009)) and PCR coupled to ligase detection reaction based on fluorescent microsphere (Luminex® microspheres).

Amplification techniques include in particular isothermal methods and PCR-based techniques. Isothermal techniques include such methods as nucleic acid sequence-based amplification (NASBA), loop-mediated isothermal amplification (LAMP), helicase-dependent amplification (HDA), rolling circle amplification (RCA), and strand displacement amplification (SDA), exponential amplification reaction (EX-PAR), isothermal and chimeric primer-initiated amplification of nucleic acids (ICANs), signal-mediated amplification of RNA technology (SMART) and others (see e.g. Asiello and Baeumner, Lab Chip; 11(8): 1420-1430, 2011).

Preferably, the PCR technique quantitatively measures starting amounts of DNA, cDNA, or RNA. Examples of PCR-based techniques according to the invention include techniques such as, but not limited to, quantitative PCR (Q-PCR), reverse-transcriptase polymerase chain reaction (RT-PCR), quantitative reverse-transcriptase PCR (QRT-PCR), or digital PCR. These techniques are well known and easily available technologies for those skilled in the art.

Preferably, the method is a one-step real-time RT-PCR assay, for example, as described in the Examples.

Preferably, a probe is used to detect the amplified product. The probe can be labeled with a fluorescent, radioactive, or enzymatic label. The amplified product can be detected with a specific detection chemistry such as fluorescence resonance energy transfer (FRET) probes, TAQMAN probes, molecular beacons, scorpion probes, fluorescently labeled (or other labeled) primers, lightup probes or a dye-based chemistry, DNA, PNA, LNA, or RNA including modified bases that bind to the amplified product to detect the sequence of interest.

Detection of the amplified products can be real-time (during the amplification process) or endpoint (after the amplification process). The invention allows for detection of the amplification products in the same vessel as amplification occurs.

Preferably, a DNA internal control is used to monitor the amplification reaction.

Preferably, a RNA internal control is used to monitor the reverse transcription and amplification reactions.

Primers

The primers of the invention are useful for both reverse transcription of RNA and amplification of the resultant products. The primer sequences are selective to SARS-CoV-2 within the coronaviruses and also other prevalent viruses causing respiratory diseases. The invention encompasses a set of primers, i.e., at least two primers of different orientations. Preferably, the primers are in a set of one forward primer and one reverse primer. All of the primers referred to herein can be specifically included in this set of primers.

Reverse Primers

The "reverse primer" is an anti-sense primer, which can be the primer for reverse transcription, and is conserved among coronavirus strains. Preferably, the reverse primer is specific for SARS-CoV-2.

In some embodiments, the reverse primer hybridizes to the sequence: 5'-ACAACACAACAAAGGGAG-3' (SEQ ID NO:11) and the RNA equivalent thereof or the sequence: 5'-CCTATATTAACCTTGACCAG-3' (SEQ ID NO:14) and the RNA equivalent thereof.

In a preferred embodiment, the primer for reverse transcription comprises the sequence 5'-CTCCCTTTGTTGTGTTGT-3' (SEQ ID NO: 2), or a variant thereof, and is from 15 to 21 bases in length, or comprises the sequence 5'-CTGGTCAAGGT-TAATATAGG-3' (SEQ ID NO: 5), or a variant thereof, and is from 17 to 23 bases in length. Preferably, the primer consists of the sequence 5'-CTCCCTTTGTTGTGTTGT-3' (SEQ ID NO: 2) or consists of the sequence 5'-CTGGT-CAAGGTTAATATAGG-3' (SEQ ID NO: 5).

In this context, the term "hybridizes to" refers to the ability of the primer to form a double-stranded hybrid molecule with SARS-CoV-2 RNA (i.e., comprising the RNA equivalent of SEQ ID NO:11 or 14) sufficient to produce a cDNA and to promote amplification of the cDNA under standard reverse transcription and amplification conditions such as those set forth in the example.

In various embodiments, the primer consists of or comprises the sequence: 5'-CTCCCTTTGTTGTGTTGT-3' (SEQ ID NO: 2) or 5'-CTGGTCAAGGTTAATATAGG-3' (SEQ ID NO: 5).

In various embodiments, the primer is at least 12, 13, 14, 15, 16, 17, 18, 19, 20, 21, 22, 23, 24, 25, 26, 27, 28, 29, or 30 nucleotides in length.

In various embodiments, the primer comprises the sequence: 5'-CTCCCTTTGTTGTGTTGT-3' (SEQ ID NO: 2) or 5'-CTGGTCAAGGTTAATATAGG 3' (SEQ ID NO: 5), in which at least 1, 2, 3, 4, or 5 nucleotides are added at the 5' end and/or at least 1, 2, 3, 4, or 5 nucleotides are added at the 3' end.

Forward Primers

The "forward primer" is a sense primer, which is specific for a subset of SARS-CoV-2.

In some embodiments, the forward primer hybridizes to the sequence: 5'-CAACAGGACTAAGCTCAT-3' (SEQ ID NO: 10) or the sequence: 5'-CGAAATCATACCAGTTACC-3' (SEQ ID NO:13).

In a preferred embodiment, the forward primer comprises the sequence 5'-ATGAGCTTAGTCCTGTTG-3' (SEQ ID NO: 1), or a variant thereof, that is from 15 to 21 bases in length, or comprises the sequence 5'-GGTAACTGGTAT-GATTTCG-3' (SEQ ID NO: 4), or a variant thereof, and is from 16 to 22 bases in length. Preferably, the primer consists of the sequence 5'-ATGAGCTTAGTCCTGTTG-3' (SEQ ID NO: 1) or consists of the sequence 5'-GGTAACTGGTAT-GATTTCG-3' (SEQ ID NO: 4).

In this context, the term "hybridizes to" refers to the ability of the primer to form a double-stranded hybrid molecule with SARS-CoV-2 RNA (i.e., comprising the RNA equivalent of SEQ ID NO:10 or 13) sufficient to produce a cDNA and to promote amplification of the cDNA under standard reverse transcription and amplification conditions such as those set forth in the example.

In various embodiments, the primer consists of or comprises the sequence: 5'-ATGAGCTTAGTCCTGTTG-3' (SEQ ID NO: 1) or 5'-GGTAACTGGTATGATTTCG-3' (SEQ ID NO: 4).

In various embodiments, the primer is at least 12, 13, 14, 15, 16, 17, 18, 19, 20, 21, 22, 23, 24, 25, 26, 27, 28, 29, or 30 nucleotides in length.

In various embodiments, the primer comprises the sequence: 5'-ATGAGCTTAGTCCTGTTG-3' (SEQ ID NO: 1) or 5'-GGTAACTGGTATGATTTCG 3' (SEQ ID NO: 4), in which at least 1, 2, 3, 4, or 5 nucleotides are added at the 5' end and/or at least 1, 2, 3, 4, or 5 nucleotides are added at the 3' end.

In some embodiments, the reverse and forward primers amplify a target sequence of SARS-CoV-2 RNA selected from the group consisting of the sequence SEQ ID NO: 16 and SEQ ID NO: 17 and the variants thereof comprising the addition of up to 20 consecutive nucleotides of 5' and/or 3' flanking sequence from said SARS-CoV-2 RNA or the deletion of up to 20 consecutive nucleotides at one or both ends of said sequences. The variant comprises the addition or deletion of up to 20 consecutive nucleotides (2, 3, 4, 5, 6, 7, 8, 9, 10, 11, 12, 13, 14, 15, 16, 17, 18, 19 and 20), preferably up to 15 (2, 3, 4, 5, 6, 7, 8, 9, 10, 11, 12, 13, 14, 15), up to 10 (2, 3, 4, 5, 6, 7, 8, 9, 10) or up to 5 (2, 3, 4, 5) consecutive nucleotides. The primer (reverse or forward) hybridizes to the target sequence or complement thereof and can be further extended in the presence of a nucleic acid polymerase to specifically amplify the target sequence. The primer sequence is substantially complementary to the target sequence or its complement. Substantially complementary means that the primer sequence is at least 80% identical, preferably at least 85%, 90%, 95% and 98% identical to the target sequence or its complement. The primer may comprise additional sequences (not complementary to the target sequence) at its 5' end. In some embodiments the primer comprises a sequence of at least 5, preferably 10 to 15 consecutive nucleotides which is 100% identical to the target sequence or its complement. In some more preferred embodiments, the primer sequence is 100% identical to the target sequence or its complement. Optionally, at least one primer of the pair includes a label (detectable moiety). In some more preferred embodiments, the reverse and forward primer is as described above.

Probes

The probes of the invention are useful for detection of coronavirus nucleic acids. As referred to herein, the "probe" of the invention is linked to a detectable label suitable for use in the method the invention. The probe is specific for SARS-CoV-2 strains.

A "detectable label" as used herein is a moiety, which can be detected directly or indirectly. In some embodiments, detection of the label involves directly detecting an emission of energy by the label (e.g., radioactivity, luminescence, optical). A label can also be detected indirectly by its ability to bind to or cleave another moiety, which itself may emit or absorb light of a particular wavelength (e.g., biotin, avidin, epitope tag such as the FLAG epitope, enzyme tag such as horseradish peroxidase). Preferred detectable labels include radioactive labels, fluorescent labels, chemiluminescent labels, bioluminescent labels, and epitope tags. Preferably, the probe is labelled with the fluorescent dyes 6-carboxy-fluorescein (6FAM) or hexachloro-6-carboxy-fluorescein (HEX), most preferably at the 5 'end. Preferably, the probe is labelled at its 3' end with black hole quencher 1 (BHQ1).

In a preferred embodiment, the probe hybridizes to the sequence: 5'-TACCGGCAGCACAAGACATCT-3' (SEQ ID NO:12) or the complement thereof, or to the sequence 5'-CCTGGCGTGGTTTGTATGA-3' (SEQ ID NO:15) or the complement thereof.

In preferred embodiments, the probe consists of or comprises the sequence: 5'-AGATGTCTTGTGCTGCCGGTA-3' (SEQ ID NO: 3), or a variant thereof, or the complement thereof and is at least 15, 16, 17, 18, 19, 20, 21, 22, 23, 24, 25, 26, 27, 28, 29, or 30 nucleotides long.

In preferred embodiments, the probe consists of or comprises the sequence: 5'-TCATACAAACCACGCCAGG-3' (SEQ ID NO: 6), or a variant thereof, or the complement thereof and is at least 15, 16, 17, 18, 19, 20, 21, 22, 23, 24, 25, 26, 27, 28, 29, or 30 nucleotides long.

In various embodiments, the probe is at least 15, 16, 17, 18, 19, 20, 21, 22, 23, 24, 25, 26, 27, 28, 29, or 30 nucleotides in length.

Controls

In various embodiments, the invention encompasses the inclusion of controls for the reverse transcription and/or amplification reactions. The DNA control of the invention is useful to monitor the amplification reaction.

In various embodiments, the control is an internal positive control, for example, wherein the internal positive control reverse primer comprises the sequence 5'-ATATTGCAGCAGTACGCACACA-3' (SEQ ID NO: 8), or a variant thereof, and is from 19 to 25 bases in length; and/or wherein the internal positive control forward primer comprises the sequence 5'-ACAGGTACGTTAATAGT-TAATAGCGT-3' (SEQ ID NO: 7), or a variant thereof, and is from 23 to 29 bases in length; and/or wherein the internal positive control probe comprises the sequence 5'-ACACTAGCCATCCTTACTGCGCTTCG-3' (SEQ ID NO: 9), or a variant thereof, or the complement thereof, and is from 23 to 29 bases in length.

In some embodiments, a real-time RT-PCR assay includes in addition of unknown samples:

Two negative samples bracketing unknown samples during RNA extraction (negative extraction controls); and/or Positive controls (in duplicate); when using in vitro synthesized transcripts as controls include five quantification positive controls (in duplicate) including $10^5$, $10^4$ and $10^3$ copies genome equivalent (ge) of in vitro synthesized RNA transcripts; and/or one negative amplification control.

Kits

The kits of the invention are useful for the reverse transcription of RNA, the amplification of the resultant products, and the detection of SARS-CoV-2 nucleic acids. The kits can contain reagents for each of these reactions. The kits of the invention can contain any of the primers, controls, and probes of the invention, alone or in any and all combinations.

In various embodiments, the kit comprises buffer(s), a reverse transcriptase, a DNA polymerase, dNTPs, primer(s), probe(s), and/or an internal control(s).

The primers, probes and kits according to the invention and as described above can be practiced on different samples; human and non-human animals, surfaces, soils, for diagnostic, epidemiology, surveillance, as well as to screen blood and tissue banks which may need to be tested against SARS-CoV2 as part of the screening for HIV1, HIV2, HBV, HCV, etc.

EXAMPLES

1. Detection of SARS-CoV-2

This protocol describes procedures for the detection of SARS-CoV-2 for two RdRp targets (IP2 and IP4). Based on the first sequences of SARS-CoV-2 made available on the GISAID database on Jan. 11, 2020 (SEQ ID NO: 19), primers and probes (nCoV_IP2 and nCoV_IP4) were designed to target the RdRp gene spanning nt 12621-12727 and 14010-14116 (positions according SARS-CoV, NC_004718). These positions correspond to nt 12669-12776 and 14059-14165 in SARS-CoV-2 sequence (SEQ ID NO: 19).

As a confirmatory assay, the E gene assay from the Charité protocol was used. (Corman V M, Landt O, Kaiser M, et al. Detection of 2019 novel coronavirus (2019-nCoV) by real-time RT-PCR. Euro Surveill 2020; 25.)

A. Kits

Kit Extraction NucleoSpin Dx Virus (Macherey Nagel 740895.50).

SuperScript™ III Platinum® One-Step Quantitative RT-PCR System. (Invitrogen 1732-020.)

B. Primers and Probes

C. Nucleic Acid Extraction

RNA is extracted from specimens using the NucleoSpin Dx Virus (Macherey Nagel ref. 740895.50). RNA extracted from 100 µl of original sample, is eluted in 100 µl of elution buffer.

D. Mix Preparation for All Separate Primer/Probe Combinations

All primers and probes described below were validated under the following conditions.

RT-PCR Mix kit: Invitrogen Superscript™ III Platinum® One-Step qRT-PCR system (ref: 11732-088).

Real-time PCR equipment: LightCycler 480 (96).

Adjustments may be required for the use of other kits or other real-time PCR instruments. All Assays used the same conditions. Primer and probe sequences, as well as optimized concentrations are shown in table below. A 25µl reaction was set up containing 5µl of RNA.

| Simplex Mix | Vol (µl) | [final] |
|---|---|---|
| H$_2$O PPI | 3.60 | |
| Reaction mix 2X | 12.50 | 3 mM Mg |
| MgSO$_4$ (50 mM) | 0.40 | 0.8 mM Mg |
| Forward Primer (10 µM) | 1.00 | 0.4 µM |
| Reverse Primer (10 µM) | 1.00 | 0.4 µM |

| Name | Sequences (5'-3') | Length (bases) | PCR product size | Ref. |
|---|---|---|---|---|
| RdRp gene/nCoV_IP2 | | | | |
| nCoV_IP2-12669Fw | ATGAGCTTAGTCCTGTTG (SEQ ID NO: 1) | 18 | 108 bp | 1 |
| nCoV_IP2-12759Rv | CTCCCTTTGTTGTGTTGT (SEQ ID NO: 2) | 18 | | |
| nCoV_IP2-12696bProbe(+) | AGATGTCTTGTGCTGCCGGTA [5']Hex [3']BHQ-1 (SEQ ID NO: 3) | 21 | | |
| RdRp gene/nCoV_IP4 | | | | |
| nCoV_IP4-14059Fw | GGTAACTGGTATGATTTCG (SEQ ID NO: 4) | 19 | 107 bp | 1 |
| nCoV_IP4-14146Rv | CTGGTCAAGGTTAATATAGG (SEQ ID NO: 5) | 20 | | |
| nCoV_IP4-14084Probe(+) | TCATACAAACCACGCCAGG [5']Fam [3']BHQ-1 (SEQ ID NO: 6) | 19 | | |
| E gene/E_Sarbeco (CoVE) | | | | |
| E_Sarbeco_F1 | ACAGGTACGTTAATAGTTAATAGCGT (SEQ ID NO: 7) | 26 | 113 bp | 2 |
| E_Sarbeco_R2 | ATATTGCAGCAGTACGCACACA (SEQ ID NO: 8) | 22 | | |
| E_Sarbeco_P1 | ACACTAGCCATCCTTACTGCGCTTCG [5']Fam [3']BHQ-1 (SEQ ID NO: 9) | 26 | | |

1. National Reference Center for Respiratory Viruses, Institut Pasteur, Paris.
2. Corman VM, Landt O, Kaiser M, et al. Detection of 2019 novel coronavirus (2019-nCoV) by real-time RT-PCR. Euro Surveill 2020;25.

Primer sets nCoV_IP2 and nCoV_IP4 can be multiplexed. Both reaction mixtures are described below.

PCR amplification regions (positions according to SARS-CoV, NC_004718):

nCoV_IP2: 12621-12727. The amplicon (108 bp) has the sequence SEQ ID NO: 16 which corresponds to positions 12669-12776 in SARS-CoV-2 sequence (SEQ ID NO: 19)

nCoV_IP4: 14010-14116. The amplicon (107 bp) has the sequence SEQ ID NO: 17 which corresponds to positions 14059-14165 in SARS-CoV-2 sequence (SEQ ID NO: 19)

E gene: 26141-26253. The amplicon (113 bp) has the sequence SEQ ID NO: 18 which corresponds to positions 26249-26361 in SARS-CoV-2 sequence (SEQ ID NO: 19).

-continued

| Simplex Mix | Vol (µl) | [final] |
|---|---|---|
| Probe (10 µM) | 0.50 | 0.2 µM |
| SuperscriptIII RT/Platinum Taq Mix | 1.00 | |
| Final Volume | 20.00 | |

| Multiplex Mix (nCoV_IP2&IP4) | Vol (µl) | [final] |
|---|---|---|
| H$_2$O PPI | 1.3 | |
| Reaction mix 2X | 12.50 | 3 mM Mg |
| MgSO$_4$ (50 mM) | 0.40 | 0.8 mM Mg |

| Multiplex Mix (nCoV_IP2&IP4) | Vol (μl) | [final] |
|---|---|---|
| Forward Primer (10 μM) | 1.00 | 0.4 μM |
| Reverse Primer (10 μM) | 1.00 | 0.4 μM |
| Forward Primer (10 μM) | 1.00 | 0.4 μM |
| Reverse Primer (10 μM) | 1.00 | 0.4 μM |
| Probe (10 μM) | 0.4 | 0.16 μM |
| Probe (10 μM) | 0.4 | 0.16 μM |
| SuperscriptIII RT/Platinum Taq Mix | 1.00 | |
| Final Volume | 20.00 | |

E. Controls

Each real-time RT-PCR assay includes in addition of unknown samples:

Two negative samples bracketing unknown samples during RNA extraction (negative extraction controls).

Positive controls (in duplicate); when using in vitro synthesized transcripts as controls include five quantification positive controls (in duplicate) including $10^5$, $10^4$ and $10^3$ copies genome equivalent (ge) of in vitro synthesized RNA transcripts.

One negative amplification control.

F. Amplification cycles (Lightcycler System)

| Reverse transcription | 55° C. | 20 min | ×1 | |
|---|---|---|---|---|
| Denaturation | 95° C. | 3 min | ×1 | |
| Amplification | 95° C. | 15 sec | ×50 | Acquisition |
| | 58° C. | 30 sec | | |
| Cooling | 40° C. | 30 sec | ×1 | |

G. Sensitivity nCoV_IP and E_Sarbeco Real-Time RT-PCR

Sensitivity, in terms of 95% hit rate is about 100 copies of RNA genome equivalent per reaction (this amount of target sequences is always detected), the probability to detect lower amounts of virus decreases, but samples containing 10 copies could be detected with multiplex assay.

| RNA copies Of transcript | Multiplex (Ct values) | | Simplex (Ct values) |
|---|---|---|---|
| | nCoV_IP2 | nCoV_IP4 | E_Sarbeco |
| 1.00E+07 | 21.67 | 21.97 | 24.72 |
| 1.00E+06 | 24.97 | 25.12 | 28.19 |
| 1.00E+05 | 28.00 | 27.88 | 30.96 |
| 1.00E+04 | 31.84 | 30.51 | 33.33 |

Ct values may vary from instrument to instrument by up to 2 cycles, while the interval between two dilutions steps is constant (ΔCt).

H. Specificity

Cross-reactivity with other respiratory viruses was tested with specimens known to be positive for a panel of respiratory viruses (influenza A(H1N1)pdm09, A(H3N2), B-Victoria, B-Yamagata; influenza C; RSV A, B; hBoV; hPIV; hMPV; HRV/enterovirus; adenovirus; hCoV (HKU1, OC43, 229E and NL63); MERS-CoV. None of the tested viruses showed reactivity with PCR2 and PCR4 using the IP2 and IP4 sets of primers and probes described in the Table above.

I. Positive Control for SARS-CoV-2 Real Time RT-PCR

Positive control for real-time RT-PCR is an in vitro transcribed RNA derived from strain BetaCoV_Wuhan_WIV04_2019 (EPI_ISL_402124). The transcript contains the amplification regions of the RdRp and E gene as positive strand. Each microtube contains 1011 copies of target sequences diluted in yeast tRNA, and lyophilised.

Reconstitution of Transcribed RNA

Add 100 μl of RNase/DNAse-free H2O to obtain a solution at a concentration of 109 copies/μl. Store at −80° C. Dilute to prepare a master bank at 2×106 copies/μl. Store at −80° C.

From this prepare a working bank of reagent at 2×104 copies/μl in order to avoid freeze/thaw cycles. Working tubes may be stored at −20° C. for less than one week.

This test which is now validated on a panel of SARS-CoV-2 of 600 positive and negative patients, including asymptomatic contact individuals, individuals returning from epidemic zone, and symptomatic patients. Within symptomatic patients, as there is also a concurrent epidemic of flu in France, negative patients with the SARS-CoV2 test of the invention were confirmed to be infected by flu or other respiratory diseases. The validation of this test will now allow dispatch for diagnosis to reference hospitals in France and abroad, and within the international network of Institut Pasteur around the world.

The invention claimed is:

1. A multiplexed method for specific detection of the presence or absence of a SARS-CoV-2 RNA in a sample, comprising:
   (A) providing a sample;
   (B) subjecting the sample to a first reverse transcription reaction with a first reverse primer to generate a first cDNA copy of SARS-CoV-2 RNA in the sample, amplifying any resultant first cDNA, and detecting any first amplified product with a first probe,
   wherein the first reverse primer comprises the sequence 5'-CTCCCTTTGTTGTGTTGT-3' (SEQ ID NO: 2), or a variant thereof, and is from 15 to 21 bases in length; and/or
   wherein the first forward primer comprises the sequence 5'-ATGAGCTTAGTCCTGTTG-3' (SEQ ID NO: 1), or a variant thereof, and is from 15 to 21 bases in length; and/or
   wherein the first probe comprises the sequence 5'-AGATGTCTTGTGCTGCCGGTA-3' (SEQ ID NO: 3) or a variant thereof, or the complement thereof of either of these, and is from 18 to 24 bases in length; and
   (C) subjecting the sample to a second reverse transcription reaction with a second reverse primer to generate a second cDNA copy of SARS-CoV-2 RNA in the sample, amplifying any resultant second cDNA, and detecting any second amplified product with a second probe
   wherein the second reverse primer comprises the sequence 5'-CTGGTCAAGGTTAATATAGG-3' (SEQ ID NO: 5) or a variant thereof, and is from 17 to 23 bases in length; and/or
   wherein the second forward primer comprises the sequence 5'-GGTAACTGGTATGATTTCG-3' (SEQ ID NO: 4), or a variant thereof, and is from 16 to 22 bases in length; and/or
   wherein the second probe comprises the sequence 5'-TCATACAAACCACGCCAGG-3' (SEQ ID NO: 6), or a variant thereof, or the complement of either of these, and is from 16 to 22 bases in length.

2. The method of claim 1,
   wherein the first reverse primer consists of the sequence 5'-CTCCCTTTGTTGTGTTGT-3' (SEQ ID NO: 2); and/or
   wherein the first forward primer consists of the sequence 5'-ATGAGCTTAGTCCTGTTG-3' (SEQ ID NO: 1); and/or
   wherein the first probe consists of the sequence 5'-AGATGTCTTGTGCTGCCGGTA-3' (SEQ ID NO: 3), or the complement thereof; and/or
   wherein the second reverse primer consists of the sequence 5'-CTGGTCAAGGTTAATATAGG-3' (SEQ ID NO: 5); and/or
   wherein the second forward primer consists of the sequence 5'-GGTAACTGGTATGATTTCG-3' (SEQ ID NO: 4); and/or
   wherein the second probe consists of the sequence 5'-TCATACAAACCACGCCAGG-3' (SEQ ID NO: 6), or the complement thereof.

3. The method of claim 2,
   wherein the first reverse primer consists of the sequence 5'-CTCCCTTTGTTGTGTTGT-3' (SEQ ID NO: 2);
   wherein the first forward primer consists of the sequence 5'-ATGAGCTTAGTCCTGTTG-3' (SEQ ID NO: 1);
   wherein the first probe consists of the sequence 5'-AGATGTCTTGTGCTGCCGGTA-3' (SEQ ID NO: 3), or the complement thereof;
   wherein the second reverse primer consists of the sequence 5'-CTGGTCAAGGTTAATATAGG-3' (SEQ ID NO: 5);
   wherein the second forward primer consists of the sequence 5'-GGTAACTGGTATGATTTCG-3' (SEQ ID NO: 4); and wherein the second probe consists of the sequence 5'-TCATACAAACCACGCCAGG-3' (SEQ ID NO: 6), or the complement thereof.

4. The method of claim 1, wherein a first amplified product is detected in (B).

5. The method of claim 1, wherein a second amplified product is detected in (C).

6. The method of claim 1, wherein a first amplified product is detected in (B) and a second amplified product is detected in (C).

7. A kit for detection of SARS-CoV-2 RNA in a sample using a multiplexed amplification method, the kit comprising:
 (A) a first reverse primer, a first forward primer, and a first probe for amplifying and detecting a first amplification product,
 wherein the first reverse primer comprises the sequence 5'-CTCCCTTTGTTGTGTTGT-3' (SEQ ID NO: 2), or a variant thereof, and is from 15 to 21 bases in length; and/or
 wherein the first forward primer comprises the sequence 5'-ATGAGCTTAGTCCTGTTG-3' (SEQ ID NO: 1), or a variant thereof, and is from 15 to 21 bases in length; and/or
 wherein the first probe comprises the sequence 5'-AGATGTCTTGTGCTGCCGGTA-3' (SEQ ID NO: 3) or a variant thereof, or the complement thereof of either of these, and is from 18 to 24 bases in length; and
 (B) a second reverse primer, a second forward primer, and a second probe for amplifying and detecting a second amplification product,
 wherein the second reverse primer comprises the sequence 5'-CTGGTCAAGGTTAATATAGG-3' (SEQ ID NO: 5) or a variant thereof, and is from 17 to 23 bases in length; and/or
 wherein the second forward primer comprises the sequence 5'-GGTAACTGGTATGATTTCG-3' (SEQ ID NO: 4), or a variant thereof, and is from 16 to 22 bases in length; and/or
 wherein the second probe comprises the sequence 5'-TCATACAAACCACGCCAGG-3' (SEQ ID NO: 6), or a variant thereof, or the complement of either of these, and is from 16 to 22 bases in length;
 wherein at least one of the first reverse primer, first forward primer, first probe, second reverse primer, second forward primer, and second probe is labelled.

8. The kit of claim 7,
 wherein the first reverse primer consists of the sequence 5'-CTCCCTTTGTTGTGTTGT-3' (SEQ ID NO: 2); and/or
 wherein the first forward primer consists of the sequence 5'-ATGAGCTTAGTCCTGTTG-3' (SEQ ID NO: 1); and/or
 wherein the first probe consists of the sequence 5'-AGATGTCTTGTGCTGCCGGTA-3' (SEQ ID NO: 3), or the complement thereof;
 and/or wherein the second reverse primer consists of the sequence 5'-CTGGTCAAGGTTAATATAGG-3' (SEQ ID NO: 5); and/or
 wherein the second forward primer consists of the sequence 5'-GGTAACTGGTATGATTTCG-3' (SEQ ID NO: 4); and/or
 wherein the second probe consists of the sequence 5'-TCATACAAACCACGCCAGG-3' (SEQ ID NO: 6), or the complement thereof.

9. The kit of claim 7,
 wherein the first reverse primer consists of the sequence 5'-CTCCCTTTGTTGTGTTGT-3' (SEQ ID NO: 2);
 wherein the first forward primer consists of the sequence 5'-ATGAGCTTAGTCCTGTTG-3' (SEQ ID NO: 1);
 wherein the first probe consists of the sequence 5'-AGATGTCTTGTGCTGCCGGTA-3' (SEQ ID NO: 3), or the complement thereof;
 wherein the second reverse primer consists of the sequence 5'-CTGGTCAAGGTTAATATAGG-3' (SEQ ID NO: 5);
 wherein the second forward primer consists of the sequence 5'-GGTAACTGGTATGATTTCG-3' (SEQ ID NO: 4); and
 wherein the second probe consists of the sequence 5'-TCATACAAACCACGCCAGG-3' (SEQ ID NO: 6), or the complement thereof.

\* \* \* \* \*

SEQUENCE LISTING

<160> NUMBER OF SEQ ID NOS: 19

<210> SEQ ID NO 1
<211> LENGTH: 18
<212> TYPE: DNA
<213> ORGANISM: artificial sequence
<220> FEATURE:
<223> OTHER INFORMATION: synthetic oligonucleotide (forward primer nCoV_IP2-12669Fw)

<400> SEQUENCE: 1
atgagcttag tcctgttg                                                 18

<210> SEQ ID NO 2
<211> LENGTH: 18
<212> TYPE: DNA

```
<213> ORGANISM: artificial sequence
<220> FEATURE:
<223> OTHER INFORMATION: synthetic oligonucleotide (reverse primer
      nCoV_IP2-12759Rv)

<400> SEQUENCE: 2 ctcccttttgt tgtgttgt                                                    18

<210> SEQ ID NO 3
<211> LENGTH: 21
<212> TYPE: DNA
<213> ORGANISM: artificial sequence
<220> FEATURE:
<223> OTHER INFORMATION: synthetic oligonucleotide (probe
      nCoV_IP2-12696bProbe(+))

<400> SEQUENCE: 3
agatgtcttg tgctgccggt a                                                 21

<210> SEQ ID NO 4
<211> LENGTH: 19
<212> TYPE: DNA
<213> ORGANISM: artificial sequence
<220> FEATURE:
<223> OTHER INFORMATION: synthetic oligonucleotide (forward primer
      nCoV_IP4-14059Fw)

<400> SEQUENCE: 4
ggtaactggt atgatttcg                                                    19

<210> SEQ ID NO 5
<211> LENGTH: 20
<212> TYPE: DNA
<213> ORGANISM: artificial sequence
<220> FEATURE:
<223> OTHER INFORMATION: synthetic oligonucleotide (reverse primer
      nCoV_IP4-14146Rv)

<400> SEQUENCE: 5
ctggtcaagg ttaatatagg                                                   20

<210> SEQ ID NO 6
<211> LENGTH: 19
<212> TYPE: DNA
<213> ORGANISM: artificial sequence
<220> FEATURE:
<223> OTHER INFORMATION: synthetic oligonucleotide (probe
      nCoV_IP4-14084Probe(+))

<400> SEQUENCE: 6
tcatacaaac cacgccagg                                                    19

<210> SEQ ID NO 7
<211> LENGTH: 26
<212> TYPE: DNA
<213> ORGANISM: artificial sequence
<220> FEATURE:
<223> OTHER INFORMATION: synthetic oligonucleotide (forward primer
      E_Sarbeco_F1)

<400> SEQUENCE: 7
acaggtacgt taatagttaa tagcgt                                            26

<210> SEQ ID NO 8
<211> LENGTH: 22
<212> TYPE: DNA
<213> ORGANISM: artificial sequence
```

```
<220> FEATURE:
<223> OTHER INFORMATION: synthetic oligonucleotide (reverse primer
      E_Sarbeco_R2)

<400> SEQUENCE: 8
atattgcagc agtacgcaca ca                                              22

<210> SEQ ID NO 9
<211> LENGTH: 26
<212> TYPE: DNA
<213> ORGANISM: artificial sequence
<220> FEATURE:
<223> OTHER INFORMATION: synthetic oligonucleotide (probe E_Sarbeco_P1)

<400> SEQUENCE: 9
acactagcca tccttactgc gcttcg                                          26

<210> SEQ ID NO 10
<211> LENGTH: 18
<212> TYPE: DNA
<213> ORGANISM: artificial sequence
<220> FEATURE:
<223> OTHER INFORMATION: synthetic oligonucleotide (target sequence)

<400> SEQUENCE: 10
caacaggact aagctcat                                                   18

<210> SEQ ID NO 11
<211> LENGTH: 18
<212> TYPE: DNA
<213> ORGANISM: artificial sequence
<220> FEATURE:
<223> OTHER INFORMATION: synthetic oligonucleotide (target sequence)

<400> SEQUENCE: 11
acaacacaac aaagggag                                                   18

<210> SEQ ID NO 12
<211> LENGTH: 21
<212> TYPE: DNA
<213> ORGANISM: artificial sequence
<220> FEATURE:
<223> OTHER INFORMATION: synthetic oligonucleotide (target sequence)

<400> SEQUENCE: 12
taccggcagc acaagacatc t                                               21

<210> SEQ ID NO 13
<211> LENGTH: 19
<212> TYPE: DNA
<213> ORGANISM: artificial sequence
<220> FEATURE:
<223> OTHER INFORMATION: synthetic oligonucleotide (target sequence)

<400> SEQUENCE: 13
cgaaatcata ccagttacc                                                  19

<210> SEQ ID NO 14
<211> LENGTH: 20
<212> TYPE: DNA
<213> ORGANISM: artificial sequence
<220> FEATURE:
<223> OTHER INFORMATION: synthetic oligonucleotide (target sequence)

<400> SEQUENCE: 14
cctatattaa ccttgaccag                                                 20
```

<210> SEQ ID NO 15
<211> LENGTH: 19
<212> TYPE: DNA
<213> ORGANISM: artificial sequence
<220> FEATURE:
<223> OTHER INFORMATION: synthetic oligonucleotide (target sequence)

<400> SEQUENCE: 15
cctggcgtgg tttgtatga                                              19

<210> SEQ ID NO 16
<211> LENGTH: 108
<212> TYPE: DNA
<213> ORGANISM: artificial sequence
<220> FEATURE:
<223> OTHER INFORMATION: synthetic polynucleotide (nCoV_IP2
      amplification product)

<400> SEQUENCE: 16
atgagcttag tcctgttgca ctacgacaga tgtcttgtgc tgccggtact acacaaactg    60
cttgcactga tgacaatgcg ttagcttact acaacacaac aaagggag                108

<210> SEQ ID NO 17
<211> LENGTH: 107
<212> TYPE: DNA
<213> ORGANISM: artificial sequence
<220> FEATURE:
<223> OTHER INFORMATION: synthetic polynucleotide (nCoV_IP4
      amplification product)

<400> SEQUENCE: 17
ggtaactggt atgatttcgg tgatttcata caaaccacgc caggtagtgg agttcctgtt    60
gtagattctt attattcatt gttaatgcct atattaacct tgaccag                 107

<210> SEQ ID NO 18
<211> LENGTH: 113
<212> TYPE: DNA
<213> ORGANISM: artificial sequence
<220> FEATURE:
<223> OTHER INFORMATION: synthetic polynucleotide (E_Sarbeco
      amplification product)

<400> SEQUENCE: 18
acaggtacgt taatagttaa tagcgtactt cttttcttg ctttcgtggt attcttgcta     60
gttacactag ccatccttac tgcgcttcga ttgtgtgcgt actgctgcaa tat          113

<210> SEQ ID NO 19
<211> LENGTH: 29788
<212> TYPE: DNA
<213> ORGANISM: SARS-CoV-2

<400> SEQUENCE: 19
aggtaacaaa ccaaccaact ttcgatctct tgtagatctg ttctctaaac gaactttaaa    60
atctgtgtgg ctgtcactcg gctgcatgct tagtgcactc acgcagtata attaataact   120
aattactgtc gttgacagga cacgagtaac cgtctatct tctgcaggct gcttacggtt    180
tcgtccgtgt tgcagccgat catcagcaca tctaggtttc gtccgggtgt gaccgaaagg   240
taagatggag agccttgtcc ctggtttcaa cgagaaaaca cacgtccaac tcagtttgcc   300
tgttttacag gttcgcgacg tgctcgtacg tggctttgga gactccgtgg aggaggtctt   360
atcagaggca cgtcaacatc ttaaagatgg cacttgtggc ttagtagaag ttgaaaaagg   420

```
cgttttgcct caacttgaac agccctatgt gttcatcaaa cgttcggatg ctcgaactgc      480
acctcatggt catgttatgg ttgagctggt agcagaactc gaaggcattc agtacggtcg      540
tagtggtgag acacttggtg tccttgtccc tcatgtgggc gaaataccag tggcttaccg      600
caaggttctt cttcgtaaga acggtaataa aggagctggt ggccatggtt acggcgccga      660
tctaaagtca tttgacttag gcgacgagct tggcactgat ccttatgaag attttcaaga      720
aaactggaac actaaacata gcagtggtgt tacccgtgaa ctcatgcgtg agcttaacgg      780
aggggcatac actcgctatg tcgataacaa cttctgtggc cctgatggct accctcttga      840
gtgcattaaa gaccttctag cacgtgctgg taaagcttca tgcactttgt ccgaacaact      900
ggactttatt gacactaaga ggggtgtata ctgctgccgt gaacatgagc atgaaattgc      960
ttggtacacg gaacgttctg aaaagagcta tgaattgcag acaccttttg aaattaaatt     1020
ggcaaagaaa tttgacacct tcaatgggga atgtccaaat tttgtatttc ccttaaattc     1080
cataatcaag actattcaac caagggttga aaagaaaaag cttgatggct ttatgggtag     1140
aattcgatct gtctatccag ttgcgtcacc aaatgaatgc aaccaaatgt gccttttcaac    1200 tctcatgaag tgtgatcatt gtggtgaaac ttcatggcag acgggcgatt tgttaaagc     1260 cacttgcgaa ttttgtggca ctgagaattt gactaaagaa ggtgccacta cttgtggtta     1320
cttaccccaa aatgctgttg ttaaaattta ttgtccagca tgtcacaatt cagaagtagg     1380
acctgagcat agtcttgccg aataccataa tgaatctggc ttgaaaacca ttcttcgtaa     1440
gggtggtcgc actattgcct ttggaggctg tgtgttctct tatgttggtt gccataacaa     1500
gtgtgcctat tgggttccac gtgctagcgc taacataggt tgtaaccata caggtgttgt     1560
tggagaaggt tccgaaggtc ttaatgacaa ccttcttgaa atactccaaa agagaaagt     1620 caacatcaat attgttggtg actttaaact taatgaagag atcgccatta ttttggcatc    1680
tttttctgct tccacaagtg cttttgtgga aactgtgaaa ggtttggatt ataaagcatt     1740
caaacaaatt gttgaatcct gtggtaattt taaagttaca aaaggaaaag ctaaaaagg     1800 tgcctggaat attggtgaac agaaatcaat actgagtcct ctttatgcat ttgcatcaga     1860
ggctgctcgt gttgtacgat caattttctc ccgcactctt gaaactgctc aaaattctgt     1920
gcgtgtttta cagaaggccg ctataacaat actagatgga atttcacagt attcactgag     1980
actcattgat gctatgatgt tcacatctga tttggctact aacaatctag ttgtaatggc     2040
ctacattaca ggtggtgttg ttcagttgac ttcgcagtgg ctaactaaca tctttggcac     2100
tgtttatgaa aaactcaaac ccgtccttga ttggcttgaa gagaagttta aggaaggtgt     2160
agagtttctt agagacggtt gggaaattgt taaatttatc tcaacctgtg cttgtgaaat     2220
tgtcggtgga caaattgtca cctgtgcaaa ggaaattaag gagagtgttc agacattctt     2280
taagcttgta aataaatttt tggctttgtg tgctgactct atcattattg gtggagctaa     2340
acttaaagcc ttgaatttag gtgaaacatt tgtcacgcac tcaaagggat tgtacagaaa     2400
gtgtgttaaa tccagagaag aaactggcct actcatgcct ctaaaagccc caaagaaat      2460 tatcttctta gagggagaaa cacttcccac agaagtgtta acagaggaag ttgtcttgaa     2520
aactggtgat ttacaaccat tagaacaacc tactagtgaa gctgttgaag ctccattggt     2580
tggtacacca gtttgtatta acgggcttat gttgctcgaa atcaaagaca cagaaaagta    2640
ctgtgccctt gcacctaata tgatggtaac aacaatacc ttcacactca aaggcggtgc      2700
accaacaaag gttactttg tgatgacac tgtgatagaa gtgcaaggtt acaagagtgt       2760
```

```
gaatatcact tttgaacttg atgaaaggat tgataaagta cttaatgaga agtgctctgc    2820
ctatacagtt gaactcggta cagaagtaaa tgagttcgcc tgtgttgtgg cagatgctgt    2880
cataaaaact ttgcaaccag tatctgaatt acttacacca ctgggcattg atttagatga    2940
gtggagtatg gctacatact acttatttga tgagtctggt gagtttaaat tggcttcaca    3000
tatgtattgt tctttctacc ctccagatga ggatgaagaa gaaggtgatt gtgaagaaga    3060
agagtttgag ccatcaactc aatatgagta tggtactgaa gatgattacc aaggtaaacc    3120
tttggaattt ggtgccactt ctgctgctct tcaacctgaa gaagagcaag aagaagattg    3180
gttagatgat gatagtcaac aaactgttgg tcaacaagac ggcagtgagg acaatcagac    3240
aactactatt caaacaattg ttgaggttca acctcaatta gagatggaac ttacaccagt    3300
tgttcagact attgaagtga atagttttag tggttattta aaacttactg acaatgtata    3360
cattaaaaat gcagacattg tggaagaagc taaaaaggta aaaccaacag tggttgttaa    3420
tgcagccaat gtttacctta acatggagg aggtgttgca ggagccttaa ataaggctac    3480
taacaatgcc atgcaagttg aatctgatga ttacatagct actaatgac cacttaaagt    3540 gggtggtagt tgtgttttaa gcggacacaa tcttgctaaa cactgtcttc atgttgtcgg    3600
cccaaatgtt aacaaaggtg aagacattca acttcttaag agtgcttatg aaaattttaa    3660
tcagcacgaa gttctacttg caccattatt atcagctggt attttttggtg ctgaccctat    3720 acattcttta agagtttgtg tagatactgt tcgcacaaat gtctacttag ctgtctttga    3780
taaaaatctc tatgacaaac ttgtttcaag cttttggaa atgaagagtg aaaagcaagt    3840
tgaacaaaag atcgctgaga ttcctaaaga ggaagttaag ccatttataa ctgaaagtaa    3900
accttcagtt gaacagagaa aacaagatga taagaaaatc aaagcttgtg ttgaagaagt    3960
tacaacaact ctggaagaaa ctaagttcct cacagaaaac ttgttacttt atattgacat    4020
taatggcaat cttcatccag attctgccac tcttgttagt gacattgaca tcactttctt    4080
aaagaaagat gctccatata tagtgggtga tgttgttcaa gagggtgttt taactgctgt    4140
ggttatacct actaaaaagg ctggtggcac tactgaaatg ctagcgaaag ctttgagaaa    4200
agtgccaaca gacaattata taaccactta cccgggtcag ggtttaaatg gttacactgt    4260
agaggaggca aagacagtgc ttaaaaagtg taaaagtgcc ttttacattc taccatctat    4320
tatctctaat gagaagcaag aaattcttgg aactgtttct tggaatttgc gagaaatgct    4380
tgcacatgca gaagaaacac gcaaattaat gcctgtctgt gtggaaacta agccatagt    4440 ttcaactata cagcgtaaat ataagggtat taaaatacaa gagggtgtgg ttgattatgg    4500
tgctagattt tacttttaca ccagtaaaac aactgtagcg tcacttatca acacacttaa    4560
cgatctaaat gaaactcttg ttacaatgcc acttggctat gtaacacatg gcttaaattt    4620
ggaagaagct gctcggtata tgagatctct caaagtgcca gctacagttt ctgtttcttc    4680
acctgatgct gttacagcgt ataatggtta tcttacttct tcttctaaaa cacctgaaga    4740
acattttatt gaaaccatct cacttgctgg ttcctataaa gattggtcct attctggaca    4800
atctacacaa ctaggtatag aatttcttaa gagaggtgat aaaagtgtat attacactag    4860
taatcctacc acattccacc tagatggtga agttatcacc tttgacaatc ttaagacact    4920
tctttctttg agagaagtga ggactattaa ggtgtttaca acagtagaca acattaacct    4980
ccacacgcaa gttgtggaca tgtcaatgac atatggacaa cagtttggtc caacttattt    5040
ggatggagct gatgttacta aaataaaacc tcataattca catgaaggta aaacattta    5100 tgttttacct aatgatgaca ctctacgtgt tgaggctttt gagtactacc atacaactga    5160
```

```
tcctagtttt ctgggtaggt acatgtcagc attaaatcac actaaaaagt ggaaataccc    5220
acaagttaat ggtttaactt ctattaaatg ggcagataac aactgttatc ttgccactgc    5280
attgttaaca ctccaacaaa tagagttgaa gtttaatcca cctgctctac aagatgctta    5340
ttacagagca agggctggtg aagctgctaa cttttgtgca cttatcttag cctactgtaa    5400
taagacagta ggtgagttag gtgatgttag agaaacaatg agttacttgt ttcaacatgc    5460
caatttagat tcttgcaaaa gagtcttgaa cgtggtgtgt aaaacttgtg acaacagca    5520 gacaacccctt aagggtgtag aagctgttat gtacatgggc acactttctt atgaacaatt    5580
taagaaaggt gttcagatac cttgtacgtg tggtaaacaa gctacaaaat atctagtaca    5640
acaggagtca ccttttgtta tgatgtcagc accacctgct cagtatgaac ttaagcatgg    5700
tacatttact tgtgctagtg agtacactgg taattaccag tgtggtcact ataaacatat    5760
aacttctaaa gaaactttgt attgcataga cggtgcttta cttacaaagt cctcagaata    5820
caaaggtcct attacggatg ttttctacaa agaaaacagt tacacaacaa ccataaaacc    5880
agttacttat aaattggatg gtgttgtttg tacagaaatt gaccctaagt tggacaatta    5940
ttataagaaa taccattctt atttcacaga gcaaccaatt gatcttgtac caaaccaacc    6000
atatccaaac gcaagcttcg ataattttaa gtttgtatgt gataatatca aatttgctga    6060
tgatttaaac cagttaactg gttataagaa acctgcttca agagagctta aagttacatt    6120
tttccctgac ttaaatggtg atgtggtggc tattgattat aaacactaca caccctcttt    6180
taagaaagga gctaaattgt tacataaacc tattgtttgg catgttaaca atgcaactaa    6240
taaagccacg tataaaccaa atacctggtg tatacgttgt ctttggagca caaaaccagt    6300
tgaaacatca aattcgtttg atgtactgaa gtcagaggac gcgcagggaa tggataatct    6360
tgcctgcgaa gatctaaaac cagtctctga agaagtagtg gaaaatccta ccatacagaa    6420
agacgttctt gagtgtaatg tgaaaactac cgaagttgta ggagacatta tacttaaacc    6480
agcaaataat agtttaaaaa ttacagaaga ggttggccac acagatctaa tggctgctta    6540
tgtagacaat tctagtctta ctattaagaa acctaatgaa ttatctagag tattaggttt    6600 gaaaacccctt gctactcatg gtttagctgc tgttaatagt gtcccttggg atactatagc    6660
taattatgct aagcctttc ttaacaaagt tgttagtaca actactaaca tagttacacg    6720
gtgtttaaac cgtgttgtta ctaattatat gccttatttc tttacttat tgctacaatt    6780 gtgtactttt actagaagta caaattctag aattaaagca tctatgccga ctactatagc    6840
aaagaatact gttaagagtg tcagtaaatt tgtctagag gcttcattta attatttgaa    6900
gtcacctaat ttttctaaac tgataaatat tataatttgg tttttactat taagtgtttg    6960
cctaggttct ttaatctact caaccgctgc tttaggtgtt ttaatgtcta atttaggcat    7020
gccttcttac tgtactggtt acagagaagg ctatttgaac tctactaatg tcactattgc    7080
aacctactgt actggttcta taccttgtag tgtttgtctt agtggtttag attcttaga    7140 cacctatcct tctttagaaa ctatacaaat taccatttca tcttttaaat gggatttaac    7200
tgcttttggc ttagttgcag agtggttttt ggcatatatt ctttttcacta ggttttctta    7260 tgtacttgga ttggctgcaa tcatgcaatt gttttttcagc tatttgcag tacatttat    7320 tagtaattct tggcttatgt ggttaataat taatcttgta caaatggccc tgatttcagc    7380
tatggttaga atgtacatct tctttgcatc attttattat gtatggaaaa gttatgtgca    7440
tgttgtagac ggttgtaatt catcaacttg tatgatgtgt tacaaacgta atagagcaac    7500
```

```
aagagtcgaa tgtacaacta ttgttaatgg tgttagaagg tccttttatg tctatgctaa      7560
tggaggtaaa ggcttttgca aactacacaa ttggaattgt gttaattgtg atacattctg      7620
tgctggtagt acatttatta gtgatgaagt tgcgagagac ttgtcactac agtttaaaag      7680
accaataaat cctactgacc agtcttctta catcgttgat agtgttacag tgaagaatgg      7740
ttccatccat ctttactttg ataaagctgg tcaaaagact tatgaaagac attctctctc      7800
tcattttgtt aacttagaca acctgagagc taataacact aaaggttcat tgcctattaa      7860
tgttatagtt tttgatggta aatcaaaatg tgaagaatca tctgcaaaat cagcgtctgt      7920
ttactacagt cagcttatgt gtcaacctat actgttacta gatcaggcat tagtgtctga      7980
tgttggtgat agtgcggaag ttgcagttaa aatgtttgat gcttacgtta atacgttttc      8040
atcaactttt aacgtaccaa tggaaaaact caaaacacta gttgcaactg cagaagctga      8100
acttgcaaag aatgtgtcct tagacaatgt cttatctact tttatttcag cagctcggca      8160
agggtttgtt gattcagatg tagaaactaa agatgttgtt gaatgtctta aattgtcaca      8220
tcaatctgac atagaagtta ctggcgatag ttgtaataac tatatgctca cctataacaa      8280
agttgaaaac atgacacccc gtgaccttgg tgcttgtatt gactgtagtg cgcgtcatat      8340
taatgcgcag gtagcaaaaa gtcacaacat tgctttgata tggaacgtta aagatttcat      8400
gtcattgtct gaacaactac gaaaacaaat acgtagtgct gctaaaaaga ataacttacc      8460
ttttaagttg acatgtgcaa ctactagaca agttgttaat gttgtaacaa caagatagc      8520 acttaagggt ggtaaaattg ttaataattg gttgaagcag ttaattaaag ttacacttgt      8580
gttccttttt gttgctgcta ttttctattt aataacacct gttcatgtca tgtctaaaca      8640
tactgacttt tcaagtgaaa tcataggata caaggctatt gatggtggtg tcactcgtga      8700
catagcatct acagatactt gttttgctaa caaacatgct gattttgaca catggtttag      8760
ccagcgtggt ggtagttata ctaatgacaa agcttgccca ttgattgctg cagtcataac      8820
aagagaagtg ggttttgtcg tgcctggttt gcctggcacg atattacgca caactaatgg      8880 tgacttttg catttcttac ctagagtttt tagtgcagtt ggtaacatct gttacacacc      8940
atcaaaactt atagagtaca ctgactttgc aacatcagct tgtgttttgg ctgctgaatg      9000
tacaattttt aaagatgctt ctggtaagcc agtaccatat tgttatgata ccaatgtact      9060
agaaggttct gttgcttatg aaagtttacg ccctgacaca cgttatgtgc tcatggatgg      9120
ctctattatt caatttccta acacctacct tgaaggttct gttagagtgg taacaacttt      9180
tgattctgag tactgtaggc acggcacttg tgaaagatca gaagctggtg tttgtgtatc      9240
tactagtggt agatgggtac ttaacaatga ttattacaga tctttaccag gagttttctg      9300
tggtgtagat gctgtaaatt tacttactaa tatgttaca ccactaattc aacctattgg      9360
tgctttggac atatcagcat ctatagtagc tggtggtatt gtagctatcg tagtaacatg      9420
ccttgcctac tatttatga ggtttagaag agcttttggt gaatacagtc atgtagttgc      9480
ctttaatact ttactattcc ttatgtcatt cactgtactc tgtttaacac cagtttactc      9540
attcttacct ggtgtttatt ctgttattta cttgtacttg acattttatc ttactaatga      9600
tgtttctttt ttagcacata ttcagtggat ggttatgttc acacctttag taccttctg      9660 gataacaatt gcttatatca tttgtatttc cacaaagcat ttctattggt tctttagtaa      9720
ttacctaaag agacgtgtag tctttaatgg tgtttccttt agtactttg aagaagctgc      9780 gctgtgcacc ttttgttaa ataaagaaat gtatctaaag ttgcgtagtg atgtgctatt      9840
acctcttacg caatataata gatacttagc tctttataat aagtacaagt attttagtgg      9900
```

```
agcaatggat acaactagct acagagaagc tgcttgttgt catctcgcaa aggctctcaa   9960
tgacttcagt aactcaggtt ctgatgttct ttaccaacca ccacaaacct ctatcacctc  10020
agctgttttg cagagtggtt ttagaaaaat ggcattccca tctggtaaag ttgagggttg  10080
tatggtacaa gtaacttgtg gtacaactac acttaacggt ctttggcttg atgacgtagt  10140
ttactgtcca agacatgtga tctgcacctc tgaagacatg cttaacccta attatgaaga  10200
tttactcatt cgtaagtcta atcataattt cttggtacag gctggtaatg ttcaactcag  10260
ggttattgga cattctatgc aaaattgtgt acttaagctt aaggttgata cagccaatcc  10320
taagacacct aagtataagt tgttcgcat tcaaccagga cagactttt cagtgttagc  10380
ttgttacaat ggttcaccat ctggtgttta ccaatgtgct atgaggccca atttcactat  10440
taagggttca ttccttaatg gttcatgtgg tagtgttggt tttaacatag attatgactg  10500
tgtctctttt tgttacatgc accatatgga attaccaact ggagttcatg ctggcacaga  10560
cttagaaggt aacttttatg dacctttgt tgacaggcaa acagcacaag cagctggtac  10620
ggacacaact attacagtta atgttttagc ttggttgtac gctgctgtta taatggaga  10680
caggtggttt ctcaatcgat ttaccacaac tcttaatgac tttaaccttg tggctatgaa  10740
gtacaattat gaacctctaa cacaagacca tgttgacata ctaggacctc tttctgctca  10800
aactggaatt gccgttttag atatgtgtgc ttcattaaaa gaattactgc aaaatggtat  10860
gaatggacgt accatattgg gtagtgcttt attagaagat gaatttacac cttttgatgt  10920
tgttagacaa tgctcaggtg ttactttcca aagtgcagtg aaaagaacaa tcaagggtac  10980
acaccactgg ttgttactca caattttgac ttcactttta gttttagtcc agagtactca  11040
atggtctttg ttcttttttt tgtatgaaaa tgccttttta cctttgcta tgggtattat  11100
tgctatgtct gcttttgcaa tgatgtttgt caaacataag catgcatttc tgtttgtt  11160
tttgttacct tctcttgcca ctgtagctta ttttaatatg gtctatatgc ctgcagttg  11220
ggtgatgcgt attatgacat ggttggatat ggttgatact agttgtctg gtttttaagct  11280
aaaagactgt gttatgtatg catcagctgt agtgttacta atccttatga cagcaagaac  11340
tgtgtatgat gatggtgcta ggagagtgtg gacacttatg aatgtcttga cactcgttta  11400
taaagtttat tatggtaatg ctttagatca agccatttcc atgtgggctc ttataatctc  11460
tgttacttct aactactcag gtgtagttac aactgtcatg ttttttggcca gaggtattgt  11520
ttttatgtgt gttgagtatt gcccctatttt cttcataact ggtaatacac ttcagtgtat  11580
aatgctagtt tattgtttct taggctattt ttgtacttgt tactttggcc tcttttgttt  11640
actcaaccgc tactttagac tgactcttgg tgtttatgat tacttagttt ctacacagga  11700
gtttagatat atgaattcac agggactact cccacccaag aatagcatag atgccttcaa  11760
actcaacatt aaattgttgg gtgttggtgg caaaccttgt atcaaagtag ccactgtaca  11820
gtctaaaatg tcagatgtaa agtgcacatc agtagtctta ctctcagttt tgcaacaact  11880
cagagtagaa tcatcatcta aattgtgggc tcaatgtgtc cagttacaca atgacattct  11940
cttagctaaa gatactactg aagcctttga aaaatggtt tcactacttt ctgttttgct  12000
ttccatgcag ggtgctgtag acataaacaa gcttgtgaa gaaatgctgg acaacagggc  12060
aaccttacaa gctatagcct cagagtttag ttcccttcca tcatatgcag cttttgctac  12120
tgctcaagaa gcttatgagc aggctgttgc taatggtgat tctgaagttg ttcttaaaaa  12180
gttgaagaag tcttttgaatg tggctaaatc tgaatttgac cgtgatgcag ccatgcaacg  12240
```

```
taagttggaa aagatggctg atcaagctat gacccaaatg tataaacagg ctagatctga  12300
ggacaagagg gcaaaagtta ctagtgctat gcagacaatg cttttcacta tgcttagaaa  12360
gttggataat gatgcactca acaacattat caacaatgca agagatggtt gtgttccctt  12420
gaacataata cctcttacaa cagcagccaa actaatggtt gtcataccag actataacac  12480
atataaaaat acgtgtgatg gtacaacatt tacttatgca tcagcattgt gggaaatcca  12540
acaggttgta gatgcagata gtaaaattgt tcaacttagt gaaattagta tggacaattc  12600
acctaattta gcatggcctc ttattgtaac agctttaagg gccaattctg ctgtcaaatt  12660
acagaataat gagcttagtc ctgttgcact acgacagatg tcttgtgctg ccggtactac  12720
acaaactgct tgcactgatg acaatgcgtt agcttactac aacacaacaa agggaggtag  12780
gtttgtactt gcactgttat ccgatttaca ggatttgaaa tgggctagat tccctaagag  12840
tgatggaact ggtactatct atacagaact ggaaccacct tgtaggtttg ttacagacac  12900
acctaaaggt cctaaagtga agtatttata ctttattaaa ggattaaaca acctaaatag  12960
aggtatggta cttggtagtt tagctgccac agtacgtcta caagctggta atgcaacaga  13020
agtgcctgcc aattcaactg tattatcttt ctgtgctttt gctgtagatg ctgctaaagc  13080
ttacaaagat tatctagcta gtgggggaca accaatcact aattgtgtta agatgttgtg  13140
tacacacact ggtactggtc aggcaataac agttacaccg gaagccaata tggatcaaga  13200
atcctttggt ggtgcatcgt gttgtctgta ctgccgttgc cacatagatc atccaaatcc  13260
taaaggattt tgtgacttaa aaggtaagta tgtacaaata cctacaactt gtgctaatga  13320
ccctgtgggt tttacactta aaaacacagt ctgtaccgtc tgcggtatgt ggaaaggtta  13380
tggctgtagt tgtgatcaac tccgcgaacc catgcttcag tcagctgatg cacaatcgtt  13440
tttaaacggg tttgcggtgt aagtgcagcc cgtcttacac cgtgcggcac aggcactagt  13500
actgatgtcg tatacagggc ttttgacatc tacaatgata agtagctgg ttttgctaaa  13560
ttcctaaaaa ctaattgttg tcgcttccaa gaaaaggacg aagatgacaa tttaattgat  13620
tcttactttg tagttaagag acacactttc tctaactacc aacatgaaga aacaatttat  13680
aatttactta aggattgtcc agctgttgct aaacatgact tctttaagtt tagaatagac  13740
ggtgacatgg taccacatat atcacgtcaa cgtcttacta aatacacaat ggcagacctc  13800
gtctatgctt taaggcattt tgatgaaggt aattgtgaca cattaaaaga atacttgtc  13860
acatacaatt gttgtgatga tgattatttc aataaaaagg actggtatga ttttgtagaa  13920
aacccagata tattacgcgt atacgccaac ttaggtgaac gtgtacgcca agctttgtta  13980
aaaacagtac aattctgtga tgccatgcga aatgctggta ttgttggtgt actgacatta  14040
gataatcaag atctcaatgg taactggtat gatttcggtg atttcataca aaccacgcca  14100
ggtagtggag ttcctgttgt agattcttat tattcattgt taatgcctat attaaccttg  14160
accagggctt taactgcaga gtcacatgtt gacactgact aacaaagcc ttacattaag  14220
tgggatttgt taaaatatga cttcacggaa gagaggttaa aactctttga ccgttatttt  14280
aaatattggg atcagacata ccacccaaat gtgttaact gtttggatga cagatgcatt  14340
ctgcattgtg caaactttaa tgttttattc tctacagtgt tcccacctac aagttttgga  14400
ccactagtga gaaaaatatt tgttgatggt gttccatttg tagtttcaac tggataccac  14460
ttcagagagc taggtgttgt acataatcag gatgtaaact acatagctc tagacttagt  14520
tttaaggaat tacttgtgta tgctgctgac cctgctatgc acgctgcttc tggtaatcta  14580
ttactagata aacgcactac gtgcttttca gtagctgcac ttactaacaa tgttgctttt  14640
```

```
caaactgtca aacccggtaa ttttaacaaa gacttctatg actttgctgt gtctaagggt   14700
ttctttaagg aaggaagttc tgttgaatta aaacacttct tctttgctca ggatggtaat   14760
gctgctatca gcgattatga ctactatcgt tataatctac caacaatgtg tgatatcaga   14820
caactactat ttgtagttga agttgttgat aagtactttg attgttacga tggtggctgt   14880
attaatgcta accaagtcat cgtcaacaac ctagacaaat cagctggttt tccatttaat   14940
aaatggggta aggctagact ttattatgat tcaatgagtt atgaggatca agatgcactt   15000
ttcgcatata caaaacgtaa tgtcatccct actataactc aaatgaatct taagtatgcc   15060
attagtgcaa agaatagagc tcgcaccgta gctggtgtct ctatctgtag tactatgacc   15120
aatagacagt ttcatcaaaa attattgaaa tcaatagccg ccactagagg agctactgta   15180
gtaattggaa caagcaaatt ctatggtggt tggcacaaca tgttaaaaac tgtttatagt   15240
gatgtagaaa accctcacct tatgggttgg gattatccta aatgtgatag agccatgcct   15300
aacatgctta gaattatggc ctcacttgtt cttgctcgca acatacaac gtgttgtagc    15360
ttgtcacacc gtttctatag attagctaat gagtgtgctc aagtattgag tgaaatggtc   15420
atgtgtggcg gttcactata tgttaaacca ggtggaacct catcaggaga tgccacaact   15480
gcttatgcta atagtgtttt taacatttgt caagctgtca cggccaatgt taatgcactt   15540
ttatctactg atggtaacaa aattgccgat aagtatgtcc gcaatttaca acacagactt   15600
tatgagtgtc tctatagaaa tagagatgtt gacacagact tgtgaatga gttttacgca    15660
tatttgcgta acatttctc aatgatgata ctctctgacg atgctgttgt gtgtttcaat    15720
agcacttatg catctcaagg tctagtggct agcataaaga actttaagtc agttctttat   15780
tatcaaaaca atgttttat gtctgaagca aaatgttgga ctgagactga ccttactaaa    15840
ggaccctcatg aattttgctc tcaacataca atgctagtta acagggtga tgattatgtg   15900
taccttcctt acccagatcc atcaagaatc ctaggggccg gctgttttgt agatgatatc   15960
gtaaaaacag atggtacact tatgattgaa cggttcgtgt ctttagctat agatgcttac   16020
ccacttacta aacatcctaa tcaggagtat gctgatgtct ttcatttgta cttacaatac   16080
ataagaaagc tacatgatga gttaacagga cacatgttag acatgtattc tgttatgctt   16140
actaatgata cacttcaag gtattgggaa cctgagtttt atgaggctat gtacacaccg   16200
catacagtct tacaggctgt tggggcttgt gttctttgca attcacagac ttcattaaga   16260
tgtggtgctt gcatacgtag accattctta tgttgtaaat gctgttacga ccatgtcata   16320
tcaacatcac ataaattagt cttgtctgtt aatccgtatg tttgcaatgc tccaggttgt   16380
gatgtcacag atgtgactca actttactta ggaggtatga gctattattg taaatcacat   16440
aaaccaccca ttagttttcc attgtgtgct aatggacaag ttttggttt atataaaaat   16500
acatgtgttg gtagcgataa tgttactgac tttaatgcaa ttgcaacatg tgactggaca   16560
aatgctggtg attacatttt agctaacacc tgtactgaaa gactcaagct ttttgcagca   16620
gaaacgctca agctactga ggagacattt aaactgtctt atggtattgc tactgtacgt    16680
gaagtgctgt ctgacagaga attacatctt tcatgggaag ttggtaaacc tagaccacca   16740
cttaaccgaa attatgtctt tactggttat cgtgtaacta aaaacagtaa agtacaaata   16800
ggagagtaca cctttgaaaa aggtgactat ggtgatgctg ttgtttaccg aggtacaaca   16860
acttacaaat taaatgttgg tgattatttt gtgctgacat cacatacagt aatgccatta   16920
agtgcaccta cactagtgcc acaagagcac tatgttagaa ttactggctt atacccaaca   16980
```

```
ctcaatatct cagatgagtt ttctagcaat gttgcaaatt atcaaaaggt tggtatgcaa   17040
aagtattcta cactccaggg accacctggt actggtaaga gtcattttgc tattggccta   17100
gctctctact acccttctgc tcgcatagtg tatacagctt gctctcatgc cgctgttgat   17160
gcactatgtg agaaggcatt aaaatatttg cctatagata aatgtagtag aattataccc   17220
gcacgtgctc gtgtagagtg ttttgataaa ttcaaagtga attcaacatt agaacagtat   17280
gtcttttgta ctgtaaatgc attgcctgag acgacagcag atatagttgt ctttgatgaa   17340
atttcaatgg ccacaaatta tgatttgagt gttgtcaatg ccagattacg tgctaagcac   17400
tatgtgtaca ttagcgaccc tgctcaatta cctgcaccac gcacattgct aactaagggc   17460
acactagaac cagaatattt caattcagtg tgtagactta tgaaaactat aggtccagac   17520
atgttcctcg gaacttgtcg gcgttgtcct gctgaaattg ttgacactgt gagtgctttg   17580
gtttatgata ataagcttaa agcacataaa gacaaatcag ctcaatgctt taaaatgttt   17640
tataagggtg ttatcacgca tgatgtttca tctgcaatta acaggccaca ataggcgtg    17700
gtaagagaat tccttacacg taaccctgct tggagaaaag ctgtctttat ttcacctttat  17760
aattcacaga atgctgtagc ctcaaagatt ttgggactac caactcaaac tgttgattca   17820
tcacagggct cagaatatga ctatgtcata ttcactcaaa ccactgaaac agctcactct   17880
tgtaatgtaa acagatttaa tgttgctatt accagagcaa aagtaggcat actttgcata   17940
atgtctgata gagacccttta tgacaagttg caatttacaa gtcttgaaat tccacgtagg   18000
aatgtggcaa ctttacaagc tgaaaatgta acaggactct ttaaagattg tagtaaggta   18060
atcactgggt tacatcctac acaggcacct acacacctca gtgttgacac taaattcaaa   18120
actgaaggtt tatgtgttga catacctggc ataccttaag acatgaccta gaagactc     18180
atctctatga tggggtttaa aatgaattat caagttaatg gttaccctaa catgtttatc   18240
acccgcgaag aagctataag acatgtacgt gcatggattg gcttcgatgt cgagggggtgt  18300
catgctacta gagaagctgt tggtaccaat ttacctttac agctaggttt ttctacaggt   18360
gttaacctag ttgctgtacc tacaggttat gttgatacac ctaataatac agattttcc    18420
agagttagtg ctaaaccacc gcctggagat caatttaaac accttatacc acttatgtac   18480
aaaggacttc cttggaatgt agtgcgtata aagattgtac aaatgttaag tgacacactt   18540
aaaaatctct ctgacagagt cgtatttgtc ttatgggcac atggctttga gttgacatct   18600
atgaagtatt ttgtgaaaat aggacctgag cgcacctgtt gtctatgtga tagacgtgcc   18660
acatgctttt ccactgcttc agacacttat gcctgttggc atcattctat tggatttgat   18720
tacgtctata atccgtttat gattgatgtt caacaatggg gttttacagg taacctacaa   18780
agcaaccatg atctgtattg tcaagtccat ggtaatgcac atgtagctag ttgtgatgca   18840
atcatgacta ggtgtctagc tgtccacgag tgctttgtta agcgtgttga ctggactatt   18900
gaatatccta taattggtga tgaactgaag attaatgcgg cttgtagaaa ggttcaacac   18960
atggttgtta aagctgcatt attagcagac aaattcccag ttcttcacga cattggtaac   19020
cctaaagcta ttaagtgtgt acctcaagct gatgtagaat ggaagttcta tgatgcacag   19080
ccttgtagtg acaaagctta taaaatagaa gaattattct attcttatgc cacacattct   19140
gacaaattca cagatggtgt atgcctattt tggaattgca atgtcgatag atatcctgct   19200
aattccattg tttgtagatt tgacactaga gtgctatcta accttaactt gcctggttgt   19260
gatggtggca gtttgtatgt aaataaacat gcattccaca caccagcttt tgataaaagt   19320
gcttttgtta attaaaaaca attaccattt ttctattact ctgacagtcc atgtgagtct   19380
```

```
catggaaaac aagtagtgtc agatatagat tatgtaccac taaagtctgc tacgtgtata   19440
acacgttgca atttaggtgg tgctgtctgt agacatcatg ctaatgagta cagattgtat   19500
ctcgatgctt ataacatgat gatctcagct ggctttagct tgtgggttta caaacaattt   19560
gatacttata acctctggaa cacttttaca agacttcaga gtttagaaaa tgtggctttt   19620
aatgttgtaa ataagggaca ctttgatgga caacagggtg aagtaccagt ttctatcatt   19680
aataacactg tttacacaaa agttgatggt gttgatgtag aattgtttga aaataaaaca   19740
acattacctg ttaatgtagc atttgagctt tgggctaagc gcaacattaa accagtacca   19800
gaggtgaaaa tactcaataa tttgggtgtg gacattgctg ctaatactgt gatctgggac   19860
tacaaaagag atgctccagc acatatatct actattggtg tttgttctat gactgacata   19920
gccaagaaac caactgaaac gatttgtgca ccactcactg tcttttttga tggtagagtt   19980
gatggtcaag tagacttatt tagaaatgcc cgtaatggtg ttcttattac agaaggtagt   20040
gttaaaggtt tacaaccatc tgtaggtccc aaacaagcta gtcttaatgg agtcacatta   20100
attggagaag ccgtaaaaac acagttcaat tattataaga agttgatgg tgttgtccag   20160 caattacctg aaacttactt tactcagagt agaaatttac aagaatttaa acccaggagt   20220
caaatggaaa ttgatttctt agaattagct atggatgaat tcattgaacg gtataaatta   20280
gaaggctatg ccttcgaaca tatcatttat ggagatttta gtcatagtca gttaggtggt   20340
ttacatctac tgattggact agctaaacgt tttaaggaat cacctttga attagaagat   20400 tttattccta tggacagtac agttaaaaac tatttcataa cagatgcgca aacaggttca   20460
tctaagtgtg tgtgttctgt tattgattta ttacttgatg attttgttga ataataaaaa   20520
tcccaagatt tatctgtagt ttctaaggtt gtcaaagtga ctattgacta tacagaaatt   20580
tcatttatgc tttggtgtaa agatggccat gtagaaacat ttacccaaa attacaatct   20640 agtcaagcat ggcaaccagg tgttgctatg cctaatcttt acaaaatgca agaatgctta   20700
ttagaaaagt gtgaccttca aaattatggt gatagtgcaa cattacctaa aggcataatg   20760
atgaatgtcg caaaatatac tcaactgtgt caatattaa acacattaac attagctgta   20820
ccctataata tgagagttat acatttggt gctggtctg ataaaggagt tgcaccaggt   20880
acagctgttt taagacagtg gttgcctacg ggtacgctgc ttgtcgattc agatcttaat   20940
gactttgtct ctgatgcaga ttcaactttg attggtgatt gtgcaactgt acatacagct   21000
aataaatggg atctcattat tagtgatatg tacgacccta gactaaaaa tgttacaaaa   21060 gaaaatgact ctaaagaggg ttttttcact tacatttgtg ggtttataca acaaagcta   21120 gctcttggag gttccgtggc tataaagata acagaacatt cttggaatgc tgatcttat   21180 aagctcatgg gacacttcgc atggtggaca gcctttgtta ctaatgtgaa tgcgtcatca   21240
tctgaagcat ttttaattgg atgtaattat cttggcaaac cacgcgaaca aatagatggt   21300
tacgtaatgc atgcaaatta catattgg aggaatacaa atccaattca gttgtcttcc   21360
tattctttat ttgacatgag taaatttccc cttaaattaa ggggtactgc tgttatgtct   21420 ttaaagaag gtcaaatcaa tgatatgatt ttatctcttc ttagtaaagg tagacttata   21480
attagagaaa acaacagagt tgttatttct agtgatgttc ttgttaacaa ctaaacgaac   21540 aatgttgtt tttcttgttt tattgccact agtctctagt cagtgtgtta atcttacaac   21600
cagaactcaa ttaccccctg catacactaa ttctttcaca cgtggtgttt attaccctga   21660
caaagttttc agatcctcag ttttacattc aactcaggac ttgttcttac ctttcttttc   21720
```

```
caatgttact tggttccatg ctatacatgt ctctgggacc aatggtacta agaggtttga   21780
taaccctgtc ctaccattta atgatggtgt ttatttttgct tccactgaga agtctaacat   21840
aataagaggc tggattttg gtactactttt agattcgaag acccagtccc tacttattgt   21900
taataacgct actaatgttg ttattaaagt ctgtgaattt caattttgta atgatccatt   21960
tttgggtgtt tattaccaca aaaacaacaa agttggatg gaaagtgagt tcagagttta   22020
ttctagtgcg aataattgca cttttgaata tgtctctcag ccttttctta tggaccttga   22080
aggaaaacag ggtaatttca aaaatcttag ggaatttgtg tttaagaata ttgatggtta   22140
ttttaaaata tattctaagc acacgcctat taatttagtg cgtgatctcc ctcaggggtt   22200
ttcggcttta gaaccattgg tagatttgcc aataggtatt aacatcacta ggtttcaaac   22260
tttacttgct ttacatagaa gttatttgac tcctggtgat tcttcttcag gttggacagc   22320
tggtgctgca gcttattatg tgggttatct tcaacctagg acttttctat aaaatataa   22380 tgaaaatgga accattacag ttgctgtagc ctgtgcactt gaccctctct cagaaacaaa   22440
gtgtacgttg aaatccttca ctgtagaaaa aggaatctat caaacttcta actttagagt   22500
ccaaccaaca gaatctattg ttagatttcc taatattaca aacttgtgcc cttttggtga   22560
agtttttaac gccaccagat ttgcatctgt ttatgcttgg aacaggaaga gaatcagcaa   22620
ctgtgttgct gattattctg tcctatataa ttccgcatca ttttccactt ttaagtgtta   22680
tggagtgtct cctactaaat taaatgatct ctgctttact aatgtctatg cagattcatt   22740
tgtaattaga ggtgatgaag tcagacaaat cgctccaggg caaactggaa agattgctga   22800
ttataattat aaattaccag atgattttac aggctgcgtt atagcttgga attctaacaa   22860
tcttgattct aaggttggtg gtaattataa ttacctgtat agattgtttta ggaagtctaa   22920 tctcaaacct tttgagagag atatttcaac tgaaatctat caggccggta gcacaccttg   22980
taatggtgtt gaaggtttta attgttactt tccttttacaa tcatatggtt tccaacccac   23040
taatggtgtt ggttaccaac catacagagt agtagtactt tcttttgaac ttctacatgc   23100
accagcaact gtttgtggac ctaaaaagtc tactaatttg gttaaaaaca aatgtgtcaa   23160
tttcaacttc aatggtttaa caggcacagg tgttcttact gagtctaaca aaaagtttct   23220
gcctttccaa caatttggca gagacattgc tgacactact gatgctgtcc gtgatccaca   23280
gacacttgag attcttgaca ttacaccatg ttcttttggt ggtgtcagtg ttataacacc   23340
aggagcaaat acatctaacc aagttactgt tctttatcag gatgttaact gcacagaagt   23400
ccctgttgct attcatgcag atcaacttac tcctacttgg cgtgtttatt ctacaggttc   23460
taatgttttc aaaacacgtg caggctgttt aataggggct gaacatgtca caactcata   23520 tgagtgtgac atacccattg gtgcaggtat atgcgctagt tatcaaactc agactaattc   23580
tcctcggcgg gcacgaagta cagctagtca atccatcatt gcctacacta tgtcacttgg   23640
tgcagaaaat tcagttgctt actctaacaa ctctattgtc atacccacaa attttactat   23700
tagtgttacc acagaaattc taccagtgtc tatgaccaag acatcagtag attgtacaat   23760
gtacatttgt agtgattcaa ctgaatgcag caatcctttg ttacaatatg cagttttttg   23820
cacacaatta aaccgtgctt taactggaat agctgttgaa caagacaaaa acacccaaga   23880
agtttttgca caagtcaaac aaatttacaa acaccacca attaaagatt tggtggtttt   23940 taattttttca caaatattac cagatccatc aaaaccaagc aagaggtcat ttattgaaga   24000 tctactttttc aacaaagtga cacttgcaga tgctggcttc atcaaacaat atggtgattg   24060
ccttggtgat attgctgcta gagacctcat ttgtgcacaa aagtttaacg gccttactgt   24120
```

```
tttgccacct tgctcacag atgaaatgat tgctcaatac acttctgcac tgttagcggg   24180
tacaatcact tctggttgga cctttggtgc aggtgctgca ttacaaatac catttgctat   24240
gcaaatggct tataggttta atggtattag agttacacag aatgttctct atgagaacca   24300
aaaattgatt gccaaccaat ttaatagtgc tattggcaaa attcaagact cactttcttc   24360
cacagcaagt gcacttggaa aacttcaaga tgtggtcaac caaaatgcac aagctttaaa   24420
cacgcttgtt aaacaactta gctccacttt cagcacaatt tcaagtgttt taatgatat   24480 cctttcacgt cttgacaaag ttgaggctga agtgcaaatt gataggttga tcacaggcag   24540
acttcaaagt ttgcagacat atgtgactca acaattaatt agagctgcag aaatcagagc   24600
ttctgctaat cttaaggcta ctaaaatgtc agagtgtgta cttggacaat caaaaagagt   24660
tgatttttgt ggaaagggct atcatcttat gtccttccct cagtcagcac ctcatggtgt   24720
agtcttcttg catgtgactt atgtccctgc acaagaaaag aacttcacaa ctgctcctgc   24780
cacttgtcat gatggaaaag cacactttcc tcgtgaaggt gtctttgttt caaatggcac   24840
acactggttt gtaacacaaa ggaattttga tgaaccacaa atcattacta cagacaacac   24900
atttgtgtct ggtaactgtg atgttgtaat aggaattgtc aacaacacag tttatgatcc   24960
tttgcaacct gaattagact cattcaagga ggagttagat aaatatttta agaatcatac   25020
atcaccagat gttgatttag gtgacatctc tggcattaat gcttcagttg taaacattca   25080
aaaagaaatt gaccgcctca atgaggttgc caagaattta aatgaatctc tcatcgatct   25140
ccaagaactt ggaaagtatg agcagtatat aaaatggcca tggtacattt ggctaggttt   25200
tatagctggc ttgattgcca tagtaatggt gacaattatg ctttgctgta tgaccagttg   25260
ctgtagttgt ctcaagggct gttgttcttg tggatcctgc tgcaaatttg atgaagacga   25320
ctctgagcca gtgctcaaag gagtcaaatt acattacaca taaacgaact tatggatttg   25380
tttatgagaa tcttcacaat tggaactgta actttgaagc aaggtgaaat caaggatgct   25440
actccttcag attttgttcg cgctactgca acgataccga tacaagcctc actccctttc   25500
ggatggctta ttgttggcgt tgcacttctt gctgtttttc agagcgcttc caaaatcata   25560
accctcaaaa agagatggca actagcactc tccaagggtg ttcactttgt ttgcaacttg   25620
ctgttgttgt ttgtaacagt ttactcacac cttttgctcg ttgctgctgg cttgtaagcc   25680
ccttttctct atctttatgc tttagtctac ttcttgcaga gtataaactt tgtaagaata   25740
ataatgaggc tttggctttg ctggaaatgc cgttccaaaa acccattact ttatgatgcc   25800
aactattttc tttgctggca tactaattgt tatgactatt gtataccttg caatagtgta   25860
acttcttcaa ttgtcattac ttcaggtgat ggcacaacaa gtcctatttc tgaacatgac   25920
taccagattg tggttatac tgaaaaatgg gaatctggag taaaagactg tgttgtatta   25980
cacagttact tcacttcaga ctattaccag ctgtactcaa ctcaattgag tacagacact   26040
ggtgttgaac atgttacctt cttcatctac aataaaattg ttgatgagcc tgaagaacat   26100
gtccaaattc acacaatcga cggttcatcc ggagttgtta atccagtaat ggaaccaatt   26160
tatgatgaac cgacgacgac tactagcgtg cctttgtaat gcacaagctg atgagtacga   26220
acttatgtac tcattcgttt cggaagagac aggtacgtta atagttaata gcgtacttct   26280
ttttcttgct ttcgtggtat tcttgctagt tacactagcc atccttactg cgcttcgatt   26340
gtgtgcgtac tgctgcaata ttgttaacgt gagtctgtta aaaccttctt tttacgttta   26400
ctctcgtgtt aaaaatctga attcttctag agttcctgat cttctggtct aaacgaacta   26460
```

```
aatattatat tagttttttct gtttggaact ttaattttag ccatggcaga ttccaacggt    26520
actattaccg ttgaagagct taaaaagctc cttgaacaat ggaacctagt aataggtttc    26580
ctattcctta catggatttg tcttctacaa tttgcctatg ccaacaggaa taggttttg    26640 tatataatta agttaatttt cctctggctg ttatggccag taactttagc ttgttttgtg    26700
cttgctgctg tttacagaat aaattggatc accggtggaa ttgctatcgc aatggcttgt    26760
cttgtaggct tgatgtggct cagctacttc attgcttctt tcagactgtt tgcgcgtacg    26820
cgttccatgt ggtcattcaa tccagaaact aacattcttc tcaacgtgcc actccatggc    26880
actattctga ccagaccgct tctagaaagt gaactcgtaa tcggagctgt gatccttcgt    26940
ggacatcttc gtattgctgg acaccatcta ggacgctgtg acatcaagga cctgcctaaa    27000
gaaatcactg ttgctacatc acgaacgctt tcttattaca aattgggagc ttcgcagcgt    27060
gtagcaggtg actcaggttt tgctgcatac agtcgctaca ggattggcaa ctataaatta    27120
aacacagacc attccagtag cagtgacaat attgctttgc ttgtacagta agtgacaaca    27180
gatgtttcat ctcgttgact ttcaggttac tatagcagag atattactaa ttattatgag    27240
gacttttaaa gtttccattt ggaatcttga ttacatcata aacctcataa ttaaaaattt    27300
atctaagtca ctaactgaga ataaatattc tcaattagat gaagagcaac caatggagat    27360
tgattaaacg aacatgaaaa ttattctttt cttggcactg ataacactcg ctacttgtga    27420
gctttatcac taccaagagt gtgttagagg tacaacagta cttttaaaag aaccttgctc    27480
ttctggaaca tacgagggca attcaccatt tcatcctcta gctgataaca aatttgcact    27540
gacttgcttt agcactcaat ttgcttttgc ttgtcctgac ggcgtaaaac acgtctatca    27600
gttacgtgcc agatcagttt cacctaaact gttcatcaga caagaggaag ttcaagaact    27660
ttactctcca atttttctta ttgttgcggc aatagtgttt ataacacttt gcttcacact    27720
caaaagaaag acagaatgat tgaactttca ttaattgact tctatttgtg ctttttagcc    27780
tttctgctat tccttgtttt aattatgctt attatctttt ggttctcact tgaactgcaa    27840
gatcataatg aaacttgtca cgcctaaacg aacatgaaat ttcttgtttt cttaggaatc    27900
atcacaactg tagctgcatt tcaccaagaa tgtagtttac agtcatgtac gcaatatcaa    27960
ccacatgtag ttgatgaccc cgtgtcctat tcacttctat ctaaatggta tattagagta    28020
ggagctagaa aatcagcacc tttaattgaa ttgtgcgtgg atgaggctgg ttctaaatca    28080
cccattcagt acatcgatat cggtaattat acagtttcct gtttaccttt tacaattaat    28140
tgccaggaac ctaaattggg tagtcttgta gtgcgttgtt cgttctatga agacttttta    28200
gagtatcatg acgttcgtgt tgttttagat ttcatctaaa cgaacaaact aaaatgtctg    28260
ataatggacc ccaaaatcag cgaaatgcac cccgcattgc ttttggtgga ccctcagatt    28320
caactggcag taaccagaat ggagaacgca gtggggcgcg atcaaaacaa cgtcggcccc    28380
aaggtttacc caataatact gcgtcttggt tcaccgctct cactcaacat ggcaaggaag    28440
accttaaatt ccctcgagga caaggcgttc aattaacac caatagcagt ccagatgacc    28500
aaattggcta ctaccgaaga gctaccagac gaattcgtgg tggtgacggt aaaatgaaag    28560
atctcagtcc aagatggtat ttctactacc taggaactgg gccagaagct ggacttccct    28620
atggtgctaa caaagacggc atcatatggg ttgcaactga gggagccttg aatacaccaa    28680
aagatcacat tggcacccgc aatcctgcta acaatgctgc aatcgtgcta caacttcctc    28740
aaggaacaac attgccaaaa ggcttctacg cagaagggag cagaggcggc agtcaagcct    28800
cttctcgttc ctcatcacgt agtcgcaaca gttcaagaaa ttcaactcca ggcagcagta    28860
```

```
ggggaacttc tcctgctaga atggctggca atggcggtga tgctgctctt gctttgctgc    28920
tgcttgacag attgaaccag cttgagagca aaatgtctgg taaaggccaa caacaacaag    28980
gccaaactgt cactaagaaa tctgctgctg aggcttctaa gaagcctcgg caaaaacgta    29040
ctgccactaa agcatacaat gtaacacaag ctttcggcag acgtggtcca gaacaaaccc    29100
aaggaaattt tggggaccag gaactaatca gacaaggaac tgattacaaa cattggccgc    29160
aaattgcaca atttgccccc agcgcttcag cgttcttcgg aatgtcgcgc attggcatgg    29220
aagtcacacc ttcgggaacg tggttgacct acacaggtgc catcaaattg gatgacaaag    29280
atccaaattt caaagatcaa gtcatttttgc tgaataagca tattgacgca tacaaaacat    29340
tcccaccaac agagcctaaa aaggacaaaa agaagaaggc tgatgaaact caagccttac    29400
cgcagagaca gaagaaacag caaactgtga ctcttcttcc tgctgcagat ttggatgatt    29460
tctccaaaca attgcaacaa tccatgagca gtgctgactc aactcaggcc taaactcatg    29520
cagaccacac aaggcagatg ggcaatacaa acgttttcgc ttttccgttt acgatatata    29580
gtctactctt gtgcagaatg aattctcgta actacatagc acaagtagat gtagttaact    29640
ttaatctcac atagcaatct ttaatcagtg tgtaacatta gggaggactt gaaagagcca    29700
ccacattttc accgaggcca cgcggagtac gatcgagtgt acagtgaaca atgctaggga    29760
gagctgccta tatggaagag ccctaatg                                      29788
```